(12) United States Patent
Zhang et al.

(10) Patent No.: US 8,527,064 B2
(45) Date of Patent: Sep. 3, 2013

(54) SYSTEM FOR STIMULATING AUTONOMIC TARGETS FROM PULMONARY ARTERY

(75) Inventors: Yunlong Zhang, Mounds View, MN (US); Haresh G. Sachanandani, Los Angeles, CA (US); Dan Li, Shoreview, MN (US); Bin Mi, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1016 days.

(21) Appl. No.: 12/327,601

(22) Filed: Dec. 3, 2008

(65) Prior Publication Data

US 2009/0228078 A1 Sep. 10, 2009

Related U.S. Application Data

(60) Provisional application No. 61/013,211, filed on Dec. 12, 2007.

(51) Int. Cl.
*A61N 1/36* (2006.01)
(52) U.S. Cl.
USPC .................. 607/116; 607/62; 607/40; 607/36
(58) Field of Classification Search
USPC ........................................ 607/62, 116, 40, 36
See application file for complete search history.

(56) References Cited

U.S. PATENT DOCUMENTS

| | | |
|---|---|---|
| 3,650,277 A | 3/1972 | Sjostrand et al. |
| 4,730,619 A | 3/1988 | Koning et al. |
| 5,144,960 A | 9/1992 | Mehra et al. |
| 5,199,428 A | 4/1993 | Obel et al. |
| 5,203,326 A | 4/1993 | Collins |
| 5,243,980 A | 9/1993 | Mehra |
| 5,334,221 A | 8/1994 | Bardy |
| 5,403,351 A | 4/1995 | Saksena |

(Continued)

FOREIGN PATENT DOCUMENTS

| | | |
|---|---|---|
| CN | 1819855 A | 8/2006 |
| WO | WO-03/011388 A2 | 2/2003 |

(Continued)

OTHER PUBLICATIONS

"U.S. Appl. No. 11/125,997, Non-Final Office Action mailed Sep. 10, 2008", 9 pgs.

(Continued)

*Primary Examiner* — George Manuel
*Assistant Examiner* — Alyssa M Alter
(74) *Attorney, Agent, or Firm* — Schwegman Lundberg & Woessner, P.A.

(57) ABSTRACT

Various implantable medical device embodiments stimulate an autonomic neural target from within a pulmonary artery, and comprise at least one electrode, a power supply, a neural stimulator connected to the power supply, and an anchor structure. The neural stimulator is configured to generate a neural stimulation signal for delivery to the neural stimulation target through the at least one electrode. The anchor structure is configured to chronically and securely implant the neural stimulator, the power supply and the at least one electrode within the pulmonary artery. The anchor structure, the neural stimulator, the power supply and the at least one electrode are configured to be implanted through a pulmonary valve into the pulmonary artery. In various embodiments, the neural stimulator is configured to be operational to implement a neural stimulation protocol when chronically implanted within the pulmonary artery without a wired connection through the pulmonary valve.

23 Claims, 16 Drawing Sheets

(56) References Cited

U.S. PATENT DOCUMENTS

| | | | |
|---|---|---|---|
| 5,409,009 A | 4/1995 | Olson | |
| 5,690,681 A | 11/1997 | Geddes et al. | |
| 5,707,400 A | 1/1998 | Terry, Jr. et al. | |
| 5,769,881 A | 6/1998 | Schroeppel et al. | |
| 6,006,122 A | 12/1999 | Smits | |
| 6,073,048 A | 6/2000 | Kieval et al. | |
| 6,076,014 A | 6/2000 | Alt | |
| 6,141,588 A * | 10/2000 | Cox et al. | 607/9 |
| 6,208,894 B1 | 3/2001 | Schulman et al. | |
| 6,292,695 B1 | 9/2001 | Webster, Jr. et al. | |
| 6,470,211 B1 | 10/2002 | Ideker et al. | |
| 6,522,926 B1 | 2/2003 | Kieval et al. | |
| 6,574,512 B1 | 6/2003 | Zhang et al. | |
| 6,584,362 B1 | 6/2003 | Scheiner et al. | |
| 6,882,886 B1 | 4/2005 | Witte et al. | |
| 7,058,450 B2 | 6/2006 | Struble et al. | |
| 7,236,821 B2 | 6/2007 | Cates et al. | |
| 7,292,888 B2 | 11/2007 | Deno et al. | |
| 7,493,161 B2 | 2/2009 | Libbus et al. | |
| 7,521,322 B2 | 4/2009 | Tang et al. | |
| 7,734,348 B2 | 6/2010 | Zhang et al. | |
| 7,765,000 B2 | 7/2010 | Zhang et al. | |
| 2002/0026222 A1 | 2/2002 | Schauerte et al. | |
| 2002/0026228 A1 | 2/2002 | Schauerte | |
| 2002/0188326 A1 | 12/2002 | Zheng et al. | |
| 2003/0060858 A1 | 3/2003 | Kieval et al. | |
| 2003/0078623 A1 | 4/2003 | Weinberg et al. | |
| 2003/0125770 A1 | 7/2003 | Fuimaono et al. | |
| 2003/0158584 A1 | 8/2003 | Cates et al. | |
| 2004/0199210 A1 | 10/2004 | Shelchuk | |
| 2004/0215289 A1 | 10/2004 | Fukui | |
| 2005/0010263 A1 | 1/2005 | Schauerte | |
| 2005/0143785 A1 | 6/2005 | Libbus | |
| 2005/0149127 A1 | 7/2005 | Libbus | |
| 2005/0149128 A1 | 7/2005 | Heil, Jr. et al. | |
| 2005/0149143 A1 | 7/2005 | Libbus et al. | |
| 2005/0149155 A1 * | 7/2005 | Scheiner et al. | 607/119 |
| 2005/0149156 A1 | 7/2005 | Libbus et al. | |
| 2005/0154418 A1 | 7/2005 | Kieval et al. | |
| 2005/0187584 A1 * | 8/2005 | Denker et al. | 607/5 |
| 2006/0074453 A1 | 4/2006 | Kieval et al. | |
| 2006/0217772 A1 | 9/2006 | Libbus et al. | |
| 2006/0229677 A1 | 10/2006 | Moffitt et al. | |
| 2006/0259084 A1 | 11/2006 | Zhang et al. | |
| 2006/0259085 A1 | 11/2006 | Zhang et al. | |
| 2007/0034261 A1 | 2/2007 | Eichler | |
| 2007/0038259 A1 | 2/2007 | Kieval et al. | |
| 2007/0038261 A1 | 2/2007 | Kieval et al. | |
| 2007/0060972 A1 | 3/2007 | Kieval et al. | |
| 2007/0068260 A1 | 3/2007 | Hong et al. | |
| 2007/0088221 A1 | 4/2007 | Stahmann | |
| 2007/0093875 A1 | 4/2007 | Chavan et al. | |
| 2007/0161912 A1 | 7/2007 | Zhang | |
| 2007/0191904 A1 | 8/2007 | Libbus et al. | |
| 2007/0255379 A1 | 11/2007 | Williams et al. | |
| 2007/0260285 A1 * | 11/2007 | Libbus et al. | 607/9 |
| 2010/0222832 A1 | 9/2010 | Zhang et al. | |

FOREIGN PATENT DOCUMENTS

| | | |
|---|---|---|
| WO | WO-2006/115877 A1 | 11/2006 |
| WO | WO-2007/050657 A1 | 5/2007 |
| WO | WO-2009/075750 A2 | 6/2009 |

OTHER PUBLICATIONS

"U.S. Appl. No. 11/125,997, Response filed May 27, 2008 to Non Final Office Action mailed Feb. 26, 2008", 19 pgs.

"U.S. Appl. No. 11/125,997, Response filed Jan. 12, 2009 to Non Final Office Action mailed Sep. 10, 2008", 12 pgs.

"U.S. Appl. No. 11/125,997, Advisory Action mailed Jun. 15, 2009", 3 pgs.

"U.S. Appl. No. 11/125,997, Final Office Action mailed Mar. 16, 2009", 11 pgs.

"U.S. Appl. No. 11/125,997, Non-Final Office Action mailed Feb. 26, 2008", 13 pgs.

"U.S. Appl. No. 11/125,997, Notice of Allowance mailed Oct. 6, 2009", 6 pgs.

"U.S. Appl. No. 11/125,997, Response filed May 18, 2009 to Final Office Action mailed Mar. 16, 2009", 13 pgs.

"U.S. Appl. No. 11/125,997, Response filed Jul. 16, 2009 to Advisory Action mailed Jun. 15, 2009 and Final Office Action mailed Mar. 16, 2009", 15 pgs.

"U.S. Appl. No. 11/126,097, Restriction Requirement mailed Mar. 26, 2008", 9 pgs.

"U.S. Appl. No. 11/126,097, Response filed Nov. 19, 2008 to Non Final Office Action mailed Aug. 19, 2008", 11 pgs.

"U.S. Appl. No. 11/126,097, Non-Final Office Action mailed Aug. 18, 2008", 7 pgs.

"U.S. Appl. No. 11/126,097, Notice of Allowance mailed Dec. 7, 2009", 7 pgs.

"U.S. Appl. No. 11/126,097, Response and Preliminary Amendment filed Apr. 28, 2008 to Restriction Requirement mailed Mar. 26, 2008", 13 pgs.

"U.S. Appl. No. 11/126,097, Response filed Jun. 15, 2009 to Restriction Requirement mailed May 14, 2009", 8 pgs.

"U.S. Appl. No. 11/126,097, Response filed May 4, 2009 to Final Office Action mailed Feb. 18, 2009", 11 pgs.

"U.S. Appl. No. 11/126,097, Restriction Requirement mailed May 14, 2009", 7 pgs.

"U.S. Appl. No. 11/126,097, Final Office Action mailed Feb. 18, 2009", 10 pgs.

"International Application Serial No. PCT/US2008/013306, International Search Report mailed Dec. 1, 2009", 5 pgs.

"International Application Serial No. PCT/US2008/013306, Written Opinion mailed Dec. 1, 2009", 8 pgs.

Ardell, J. L., et al., "Selective vagal innervation of sinoatrial and atrioventricular nodes in canine heart", Am. J. Physiol. Heart Circ. Physiol., 251(4, Pt 2), (1986), H764-H773.

Bevan, J. A., et al., "Action of lobeline on pulmonary artery mechanoreceptors of the cat", Circ Res., 17, (Jul. 1965), 19-29.

Coleridge, J. C, et al., "Reflex effects of stimulating baroreceptors in the pulmonary artery", J. Physiol, 166, (1963), 197-210.

Kolman, B. S., et al., "The Effect of Vagus Nerve Stimulation Upon Vulnerability of the Canine Ventricle: Role of Sympathetic-Parasympathetic Interactions", Circulation, 52(4), (1975), 578-585.

McMahon, N. C., et al., "Reflex responses from the main pulmonary artery and bifurcation in anaesthetised dogs.", Experimental Physiology, 85(4), (2000), 411-420.

Moore, J. P., et al., "Pulmonary arterial distension and vagal afferent nerve activity in anaesthetized dogs", J Physiol., 555(Pt 3), (Mar. 16, 2004), 805-14.

Murakawa, Y., et al., "Effect of Cervical Vagal Nerve stimulation on Defibrillation Energy: a Possible Adjunct to Efficient Defibrillation", Japanese Heart Journal, 44(1), (Jan. 2003), 91-100.

Nishi, K., et al., "Afferent fibres from pulmonary arterial baroreceptors in the left cardiac sympathetic nerve of the cat", J Physiol., 240(1), (Jul. 1974), 53-66.

"U.S. Appl. No. 11/125,997, Notice of Allowance mailed Jan. 28, 2010", 7 pgs.

"U.S. Appl. No. 11/126,097, Notice of Allowance mailed Mar. 24, 2010", 4 pgs.

"European Application Serial No. 08858726.2, Comminication mailed Jul. 20, 2010", 1 pg.

"European Application Seriai No. 08858726.2, Response filed Aug. 17, 2010 to Communication mailed Jul. 20, 2010", 6 pgs.

Schauerte, P. N, et al., "Transvenous parasympathetic cardiac nerve stimulation: an approach for stable sinus rate control", Journal of Cardiovascular Electrophysiology, 10(11), (Nov. 1999), 1517-1524.

Schauerte, P., et al., "Ventricular Rate Control During Atrial Fibrillation by Cardiac Parasympathetic Nerve Stimulation: A Transvenous Approach", J. Am. Coll. Cardiol., 34 (7), (Dec. 1999), 2043-2050.

Scherlag, B. J, et al., "Endovascular stimulation within the left pulmonary artery to induce slowing of heart rate and paroxysmal atrial fibrillation.", Cardiovasc Research, 54(2), (May 2002), 470-475.

"Australian Application Serial No. 2008336077, Office Action mailed Sep. 6, 2011", 4 pgs.

"International Application Serial No. PCT/US2008/013306, International Preliminary Report on Patentability mailed Jun. 24, 2010", 10 pgs.

"U.S. Appl. No. 12/779,177, Response filed Jul. 31, 2012 to Non Final Office Action mailed May 17, 2012", 7 pgs.

"U.S. Appl. No. 12/779,177, Non Final Office Action mailed May 17, 2012", 7 pgs.

"Australian Application Serial No. 2008336077, Second Examiners Report mailed May 15, 2012", 3 pgs.

"Japanese Application Serial No. 2010-537932, Office Action mailed May 15, 2012", (w/ English Translation) 9 pgs.

"Japanese Application Serial No. 2010-537932, Response filed Aug. 10, 2012 to Office Action mailed May 15, 2012", (w/ English Translation of Amended Claims), 11 pgs.

"Australian Application No. 2008336077, Third Examination Report dated Oct. 24, 2012", 4 pgs.

"Australian Application Serial No. 2008336077, Response filed Aug. 22, 2012 to Second Examiners Report mailed May 15, 2012", 4 pgs.

"Chinese Application Serial No. 200880126462.0, Office Action mailed Aug. 24, 2012", With English Translation, 12 pgs.

"Japanese Application Serial No. 2010-537932, Office Action mailed Sep. 11, 2012", With English Translation, 4 pgs.

"U.S. Appl. No. 12/779,177, Notice of Allowance mailed Dec. 10, 2012", 7 pgs.

"Japanese Application Serial No. 2010-537932,Response filed Dec. 10, 2012 to Office Action mailed Sep. 11, 2012", (w/ English Translation of Claims), 10 pgs.

"Australian Application Serial No. 2008336077, Response filed Mar. 27, 2012 to Office Action mailed Sep. 6, 2011", 19 pgs.

* cited by examiner

SYSTEM FOR STIMULATING AUTONOMIC TARGETS FROM PULMONARY ARTERY

CROSS-REFERENCE TO RELATED APPLICATION

This application claims the benefit of U.S. Provisional Application No. 61/013,211, filed on Dec. 12, 2007, under 35 U.S.C. § 119(e), which is hereby incorporated by reference.

TECHNICAL FIELD

This application relates generally to medical devices and, more particularly, to systems, devices and methods for stimulating autonomic targets, such as pulmonary artery baroreceptors, from within the pulmonary artery.

BACKGROUND

High sympathetic tone, also referred to as autonomic imbalance, is a character of many heart diseases, especially in heart failure (HF) and acute myocardial infarction (AMI). β-blockers are the primary medication to counter balance the increased sympathetic activities. The autonomic system controls physiological activities of the body and the imbalance of autonomic tone is related to many diseases and conditions. Vagal stimulation is an electrophysiological approach to counter balance autonomic imbalance.

Neural stimulation has been the subject of a number of studies and has been proposed to treat sleep disorders, gastrointestinal motility, eating disorders, obesity, anorexia, gastrointestinal tract disorders, hypertension, coma, and epilepsy. Electrical stimulation of parasympathetic nerves can elicit the baroreflex, inducing a reduction of sympathetic nerve activity and reducing blood pressure by decreasing vascular resistance. The baroreflex naturally starts from receptors. Vagal afferent fibers, for example, innervate and mediate the baroreflex. Parasympathetic stimulation counteracts sympathetic activity, which further reduces heart rate and blood pressure. In a congestive heart failure (CHF) patient, the patient's sympathetic tone increases and catecholamine increase. Increased sympathetic tone and catecholamine can cause increased cardiac oxygen consumption, cardiac hypertrophy (remodeling), worsening heart failure, and sudden cardiac death. Vagus nerve stimulation may antagonize sympathetic tone, and may prevent sudden cardiac death. The vagal stimulation counteracts the high sympathetic tone associated with CHF, resulting in a decreased heart rate, reduced oxygen demand, increased diastolic period, and reduced incidence of ventricular arrhythmia. A decrease in the sympathetic tone decreases the excitability of the heart, which decreases arrhythmias. Modulation of the sympathetic and parasympathetic nervous system with neural stimulation has been shown to have positive clinical benefits, such as protecting the myocardium from further remodeling and predisposition to fatal arrhythmias following a myocardial infarction.

SUMMARY

Various implantable medical device embodiments stimulate an autonomic neural target from within a pulmonary artery, and comprise at least one electrode, a power supply, a neural stimulator connected to the power supply, and an anchor structure. The neural stimulator is configured to generate a neural stimulation signal for delivery to the neural stimulation target through the at least one electrode. The anchor structure is configured to chronically and securely implant the neural stimulator, the power supply and the at least one electrode within the pulmonary artery. The anchor structure, the neural stimulator, the power supply and the at least one electrode are configured to be implanted through a pulmonary valve into the pulmonary artery.

Various system embodiments stimulate baroreceptors in a pulmonary artery, and comprise means for sensing at least one physiological parameter, at least one pulmonary artery device configured to be delivered through a pulmonary valve and completely implanted in the pulmonary artery, and means for implementing a neural stimulation therapy responsive to a sensed physiological parameter. The pulmonary artery device includes a power supply for providing power to the at least one pulmonary artery device, means for stimulating the autonomic neural target from within the pulmonary artery, and means for chronically and securely implanting the at least one pulmonary artery device within the pulmonary artery.

According to various method embodiments, at least one physiological parameter is sensed, and a neural target is stimulated using a neural stimulator chronically implanted within a pulmonary artery. Stimulating the neural target includes implementing a neural stimulation therapy responsive to a sensed physiological parameter when the neural stimulator is chronically implanted within the pulmonary artery without using a wired connection through the pulmonary valve. According to various method embodiments, at least one physiological parameter is sensed, and a neural target is stimulated using a neural stimulator chronically implanted within a pulmonary artery. Stimulating the neural target includes implementing a neural stimulation therapy responsive to a sensed physiological parameter when the neural stimulator is chronically implanted within the pulmonary artery. Implementing the neural stimulation therapy includes sensing at least two physiological parameters indicative of autonomic health which can be used as a control input for delivering neural stimulation. The at least two parameters have different time responses to a change in the autonomic health such that a first physiological parameter provides an indication of autonomic health that is more acute than a second physiological parameter. Implementing the neural stimulation therapy includes generating a composite index using the at least two physiological parameters, including weighting each of the at least two physiological parameters based at least in part on each parameter's time response, and using the composite index to control delivery of the neural stimulation.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1:
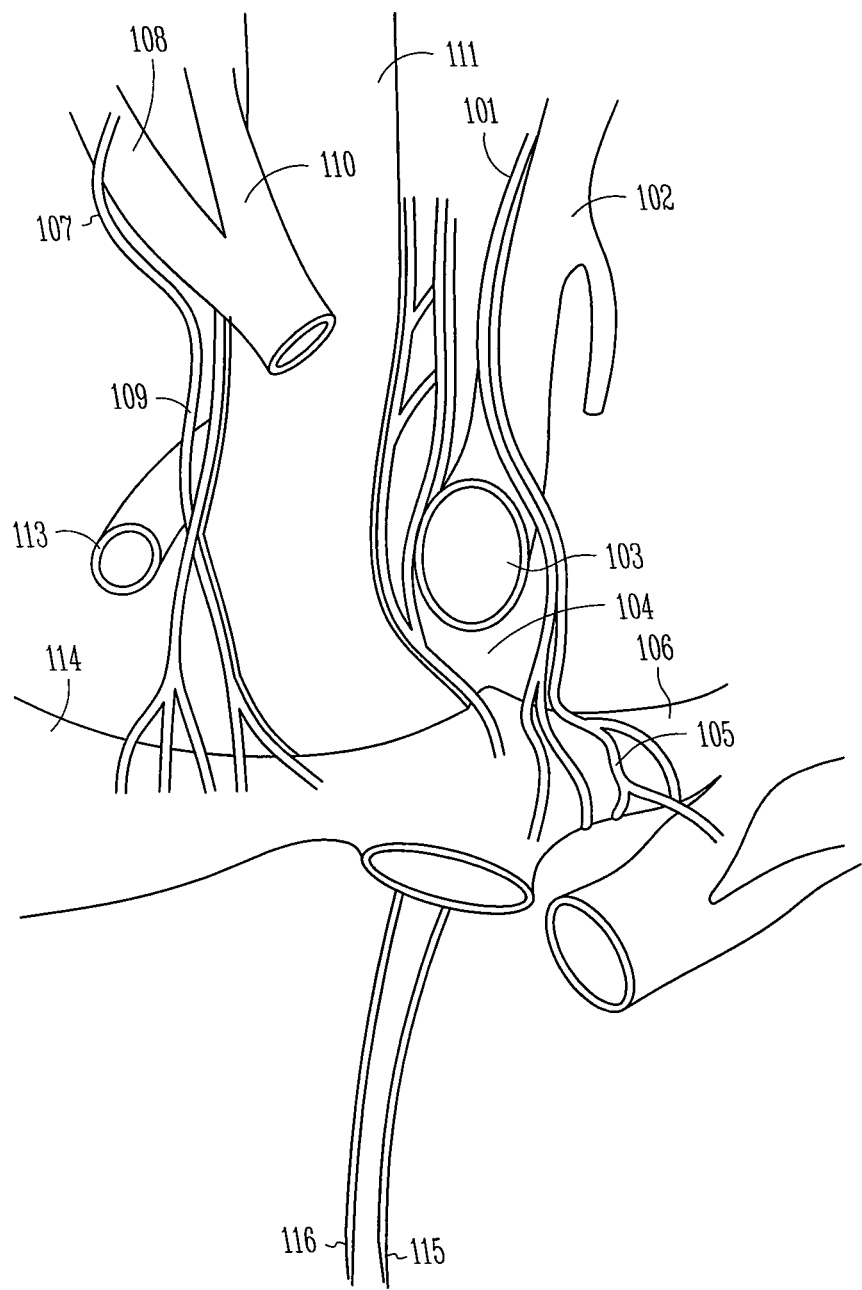
FIG. 1 illustrates physiology of the left and right pulmonary arteries and the left and right vagus nerves.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The pulmonary artery has baroreceptors in its left and right branch, and in its bifurcation region between the left and right branch. Vagal nerve afferent activity increases when these pulmonary artery baroreceptors, referred to herein as PA baroreceptors, are stimulated. When the PA baroreceptors are excited, they send inhibitory signals to cardiovascular center in the hypothalamus, which in turn decreases sympathetic output and increases vagal output. In a physiological condition, PA pressure is the primary stimulus to PA baroreceptors. PA baroreceptors respond to stimulation (e.g. electrical stimulation or other methods of stimulating a neural target), such that stimulation of a PA baroreceptor to decrease sympathetic output and increase vagal output can mimic β-blocker effect.

Various medical device embodiments detect a pathophysiological condition, such as may be detected using one or more sensors, and deliver vagal stimulation via PA baroreceptors. Some device embodiments use a pulmonary artery pressure sensor, referred to herein as a PA pressure sensor. In place of or in addition to stimulation of PA baroreceptors, other autonomic neural targets, such as some branches of the vagus nerve, pass the pulmonary arteries and may be targeted with transvascular stimulation from within the pulmonary artery.

A device embodiment is configured to be chronically implanted within a pulmonary artery by passing the device through a pulmonary valve, and includes a PA pressure sensor and at least one electrode (e.g. one or more pair electrodes or an electrode used for unipolar stimulation), an implantable control device that can be implanted subcutaneously, a control system that implements appropriate algorithms to analyze conditions that are potentially pathological and deliver a proper mode of neural stimulation therapy for the detected pathological condition, and an anchor system. A brief description of the devices components are provided below.

One embodiment of the PA device, used herein to identify a chronically implantable device configured to be securely placed in the pulmonary artery (including left and right pulmonary artery and the bifurcation region between the left and right pulmonary region), includes a self-expandable metallic mesh structure that functions as the anchor device for the PA device. The metallic mesh structure is formed using an appropriate material such as titanium nickel alloy (TiNi). The metallic structure can have one or more pair electrodes for electrical stimulation or itself can be the electrode. According to some embodiments, the PA device is anchored in the pulmonary artery using an expandable balloon that allows for substantially unobstructed flow of blood when inflated. For example, a tubular balloon can be configured for intravascular placement with a dynamically adjustable diameter. The tubular balloon can include open spaces that form lumens between fluid passageways, where the fluid passageways allow the balloon to be inflated and deflated, and the open spaces allow for the substantially unobstructed flow of blood in the vessel after the balloon is placed in the vessel. Another balloon embodiment includes a multi-lobe balloon that has spaces between the lobes that allow for substantially unobstructed flow of blood in the vessel after the balloon is placed in the vessel. Examples of non-obstructive balloons are illustrated in application Ser. No. 11/748,171, filed May 14, 2007, entitled Method and Apparatus for Regulating Blood Volume Using Volume Receptor Stimulation, which is herein incorporated by reference in its entirety. The PA device can be implanted transvenously and anchored in the right pulmonary branch and/or the left pulmonary branch. The PA device has at least one electrode.

Some PA device embodiments include a housing module that contains a PA pressure sensor, stimulation circuit, telemetry circuit, and power supply. According to other embodiments, each of the PA pressure sensor and the pacing circuit have their own housing module. Also, the PA device can be a pacing device only, and the sensing system can be a stand alone implantable system.

According to various embodiments, the PA pressure sensor is a power-efficient, Micro-Electro-Mechanical Systems (MEMS)-based capacitive pressure sensor, where an application specific integrated circuit (ASIC) circuit provides analog and digital functions to acquire the sensor input and use that as the feedback to control the electrode stimulation. A Direct Digital Synthesis (DDS) based signal generation algorithm can be used to generate special shape function pulse.

The PA device is chronically implanted within a pulmonary artery by passing the PA device from the right ventricle through the pulmonary valve and into the pulmonary artery. The PA device is operational within the pulmonary artery without a chronically-placed lead extending through the pulmonary valve between the pulmonary artery and right ventricle. As such, the function of the pulmonary valve (e.g. its ability to make a seal between the right ventricle and pulmonary artery) is not expected to be affected by the chronically-implanted PA device.

Various PA device embodiments detect heart rate using sensing electrodes, and various PA device embodiments extract heart rate from the sensed PA pressure. Some PA device embodiments obtain heart rate information from a device external to the pulmonary artery, such as an implantable cardiac rhythm management (CRM) device.

The control system can be part of a device implanted in the pulmonary artery (e.g. integrated with the PA device), or can be a device external to the pulmonary artery. Telemetry circuit and transducers can be used to communicate with external/internal devices such as an implanted ICD, wireless sensors or a communicator, and deliver the neural stimulation therapy according to a programmed protocol. The communication technology can be radio frequency, acoustic, and the like. In some embodiments, the control system is included in an implantable device (e.g. CRM device) implanted outside of the pulmonary artery. The PA module has a telemetry system and the control device works with PA module wirelessly. The control device controls neural stimulation delivery, receives measurements from sensors, and processes signals. The control device commands may include, by way of example and not limitation, start and stop neural stimulation, the number or length of a neural stimulation pulse train, the frequency of neural stimulation, the duty cycle of the simulation signal, and the therapy duration. The control device can monitor the physiological responses via its sensors, external to the pulmonary artery and/or using sensor(s) of the PA device. The physiological responses can be used to modify the configuration of the neural stimulation.

When the PA device is a pacing device only, it can be used with a control device external to the pulmonary artery with sensors such as impedance, pressure, heart sounds, respiration, flow/velocity, and/or chemical sensors. The control device analyzes the sensor data and commands the PA device to deliver neural stimulation according to a neural stimulation protocol.

According to various embodiments, the PA device is powered by a rechargeable battery. Various embodiments use a lithium battery. The rechargeable battery is connected to the sensor and/or pacing module either in one complete package or separate packages. The battery can be recharged using inductive, radio frequency or acoustic recharging technology.

The PA device can be used stimulate baroreceptors in a heart failure patient. When heart failure is worsening, PA pressure increases. The increased PA pressure triggers the PA device to deliver PA baroreceptor stimulation therapy, which in turn activate vagal output. Heart failure is characterized by autonomic nerve imbalance, specifically sympathetic tone increases. The PA baroreceptor stimulation and vagal nerve activation counteract the activated sympathetic tone. Another clinical application is to stimulate PA baroreceptors during an ischemic attack, especially in myocardial infarction (MI). Balanced autonomic activity during MI can significantly reduce its mortality. PA baroreceptor stimulation can also be used in hypertension treatment.

Various system embodiments include a PA device with a baroreceptor stimulator configured to stimulate the baroreceptors from within the pulmonary artery, and further include a sensor capable of detecting a pathological condition and/or physiological feedback for the baroreceptor stimulation, and a controller configured to implement a therapy protocol using the sensor and the baroreceptor stimulator. Some embodiments integrate the sensor with the PA device. Some embodiments chronically implant the sensor in the pulmonary artery as a separate device from the PA device that includes the baroreceptor stimulator. Some embodiments provide the sensing outside of the pulmonary artery, such as may be performed by an implantable CRM device or other implantable device.

According to various embodiments, the controller is adapted to analyze one or more signals indicative of a pathological condition or conditions, determine an appropriate therapy or therapies for a detected pathological condition or conditions, and set a sensor threshold(s) for activating the therapy. The signals indicative of the pathological condition(s) can be used to determine a baseline for the sensor. Measurements can be taken intermittently or periodically (e.g. daily) and trended (e.g. weekly or monthly trends). The therapies can include therapies triggered by an acute event, and can include chronically delivered therapies delivered according to a programmed schedule. The sensor threshold can be set empirically. The threshold for PA pressure can be a baseline, an absolute value (mmHg) deviate from a baseline pressure, or a percentage deviate from the baseline pressure. The threshold for heart rate can include an upper threshold and a lower threshold. The threshold for impedance can be a baseline, an absolute value deviate from a baseline for the impedance, or a percentage deviate from the baseline for the impedance. The threshold for respiration can be a baseline, an absolute value deviate from the baseline, or a percentage deviate from the baseline. The threshold for baroreflex sensitivity (BRS) can include an upper threshold and a lower threshold. The threshold for BRS can include a baseline, an absolute value deviate from the baseline, or a percentage deviate from the baseline. An indicator of BRS can be a slope of RR intervals plotted against systolic blood pressure, where the thresholds indicate a confidence interval. BRS is discussed in US 20070161912, entitled Assessing Autonomic Activity Using Baroreflex Analysis, which is incorporated herein by reference in its entirety. The threshold for heart sounds can be the detected occurrence of an S3 heart sound, and the threshold for ischemia can be a detected ischemia event.

Provided below, for the benefit of the reader, is a brief discussion of physiology and therapies. The disclosure continues with a discussion of various system, device and method embodiments.

Physiology

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscle around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system.

The heart rate and force are increased with an increase in sympathetic activity or decrease in parasympathetic activity, and heart rate and force is decreased with a decrease in sympathetic activity or an increase in parasympathetic activity. An afferent nerve conveys impulses toward a nerve center. An efferent nerve conveys impulses away from a nerve center.

The sympathetic and parasympathetic nervous systems have physiological effects other than heart rate and blood pressure. For example, increased sympathetic tone dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder; and increased parasympathetic tone constricts the pupil, increases saliva and mucus production, contracts the bronchial muscle, increases secretions and motility in the stomach and large intestine, increases digestion in the small intention, increases urine secretion, and contracts the wall and relaxes the sphincter of the bladder. The functions associated with the sympathetic and parasympathetic nervous systems are many and can be complexly integrated with each other. Embodiments of the present subject matter stimulate specific nerve ending that function as baroreceptors (the natural input for a baroreflex response) within the pulmonary artery to mimic the physiological response of the PA baroreceptors to PA pressure.

Baroreflex is a reflex triggered by stimulation of a baroreceptor. The baroreflex pathway involves an afferent pathway (e.g. afferent fibers in the vagus nerve or branch thereof) between baroreceptors and the brain stem, and efferent pathways (e.g. efferent fibers in the vagus nerve or branch thereof) from the brain stem to vasomotor centers (muscles and nerves that control vasodilation/vasoconstriction). A baroreceptor senses pressure changes, as it is sensitive to stretching of the wall resulting from increased pressure from within. Baroreceptors function as the receptor of the central reflex mechanism that tends to reduce that pressure. Baroreceptors are naturally stimulated by internal pressure and the stretching of the arterial wall. Stimulating baroreceptors inhibits sympathetic nerve activity (stimulates the parasympathetic nervous system) and reduces systemic arterial pressure by decreasing peripheral vascular resistance and cardiac contractility. Embodiments of the present subject matter modulate vagal activity by stimulating PA baroreceptors. Vagal modulation may be used to treat a variety of cardiovascular disorders, including but not limited to heart failure, post-MI remodeling, and hypertension. These conditions are briefly described below.

Heart failure refers to a clinical syndrome in which cardiac function causes a below normal cardiac output that can fall below a level adequate to meet the metabolic demand of tissues. Heart failure may present itself as congestive heart failure (CHF) due to the accompanying venous and pulmonary congestion. Heart failure can be due to a variety of etiologies such as ischemic heart disease, hypertension and diabetes.

Hypertension is a cause of heart disease and other related cardiac co-morbidities. Hypertension occurs when blood vessels constrict. As a result, the heart works harder to maintain flow at a higher blood pressure, which can contribute to heart failure. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 120 mm Hg or a diastolic blood pressure above 80 mm Hg. Consequences of uncontrolled hypertension include, but are not limited to, retinal vascular disease and stroke, left ventricular hypertrophy and failure, myocardial infarction, dissecting aneurysm, and renovascular disease.

Cardiac remodeling refers to a complex remodeling process of the ventricles that involves structural, biochemical, neurohormonal, and electrophysiologic factors, which can result following an MI or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. It is the combination of hemodynamics, sympathetic nervous system and hormonal alterations (such as presence or absence of angiotensin converting enzyme (ACE) activity) that ultimately account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Therapies

The present subject matter relates to systems, devices and methods for providing vagal stimulation via stimulation of PA baroreceptors or via transvascular stimulation of an autonomic neural target proximate to the pulmonary artery (e.g. a branch of the vagus nerve that passes the pulmonary artery).

FIG. 1 illustrates physiology of the left and right pulmonary arteries and the left and right vagus nerves. The pulmonary artery includes baroreceptors that are innervated by the vagus nerve. Also, various branches of the vagus nerve pass the pulmonary artery. A left vagus nerve 101 extends next to a subclavian artery 102. Various nerves extend around the arch of the aorta 103. Vagus nerve 101 also extends past the ligamentum arteriosum 104. The anterior pulmonary plexus 105 crosses the left pulmonary artery 106. Right vagus nerve 107 extends past a subclavian artery 108. Cardiac nerves 109 extend past the brachiocephalic trunk 110 near the trachea 111. Cardiac nerves 109 also extend past the arch of an azygos vein 113 to the right pulmonary artery 114. A lower portion 115 of the left vagus nerve 101 and a lower portion 116 of the right vagus nerve 107 appear in the lower portion of FIG. 1. Thus, a number of vagal targets can be targeted within the pulmonary artery, including PA baroreceptors and some vagus nerve branches.

Neural Stimulation Therapies

Vagal stimulation is an example of a neural stimulation therapy. Examples of vagal therapies include neural stimulation therapies for blood pressure control such as to treat hypertension, for cardiac rhythm management, for myocardial infarction and ischemia, for heart failure, and for conditioning. Vagal stimulation has been proposed for many other therapies such as therapies for pain, epilepsy and eating disorders. This listing of other neural stimulation therapies is not intended to be an exhaustive listing. Neural stimulation has been proposed using electrical, acoustic, ultrasound, light, and magnetic therapies.

A therapy embodiment involves preventing and/or treating ventricular remodeling using vagal stimulation through the stimulation of pulmonary artery baroreceptors or vagal targets proximate to the pulmonary artery. Activity of the autonomic nervous system is at least partly responsible for the ventricular remodeling which occurs as a consequence of an MI or due to heart failure. It has been demonstrated that remodeling can be affected by pharmacological intervention with the use of, for example, ACE inhibitors and beta-blockers. Pharmacological treatment carries with it the risk of side effects, however, and it is also difficult to modulate the effects of drugs in a precise manner. Embodiments of the present subject matter employ electrostimulatory means to modulate autonomic activity, referred to as anti-remodeling therapy (ART). When delivered in conjunction with ventricular resynchronization pacing, also referred to as remodeling control therapy (RCT), such modulation of autonomic activity may act synergistically to reverse or prevent cardiac remodeling. One neural stimulation therapy embodiment involves treating hypertension by stimulating the baroreflex for sustained periods of time sufficient to reduce hypertension using vagal stimulation through the stimulation of pulmonary artery baroreceptors or vagal targets proximate to the pulmonary artery.

Myocardial Stimulation Therapies

Various neural stimulation therapies can be integrated with various myocardial stimulation therapies. The integration of therapies may have a synergistic effect. Therapies can be synchronized with each other, and sensed data can be shared between the therapies. For example, heart rate and transthoracic impedance can be provided from a CRM device to a PA neural stimulation device. A myocardial stimulation therapy provides a cardiac therapy using electrical stimulation of the myocardium. Some examples of myocardial stimulation therapies are provided below.

A pacemaker is a device which paces the heart with timed pacing pulses, most commonly for the treatment of bradycardia where the ventricular rate is too slow. If functioning properly, the pacemaker makes up for the heart's inability to pace itself at an appropriate rhythm in order to meet metabolic demand by enforcing a minimum heart rate. Implantable devices have also been developed that affect the manner and degree to which the heart chambers contract during a cardiac cycle in order to promote the efficient pumping of blood. The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed CRT. Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

CRT can be beneficial in reducing the deleterious ventricular remodeling which can occur in post-MI and heart failure patients. Presumably, this occurs as a result of changes in the distribution of wall stress experienced by the ventricles during the cardiac pumping cycle when CRT is applied. The degree to which a heart muscle fiber is stretched before it contracts is termed the preload, and the maximum tension and velocity of shortening of a muscle fiber increases with increasing preload. When a myocardial region contracts late relative to other regions, the contraction of those opposing regions stretches the later contracting region and increases the preload. The degree of tension or stress on a heart muscle fiber as it contracts is termed the afterload. Because pressure within the ventricles rises rapidly from a diastolic to a systolic value as blood is pumped out into the aorta and pulmonary arteries, the part of the ventricle that first contracts due to an excitatory stimulation pulse does so against a lower afterload than does a part of the ventricle contracting later. Thus a myocardial region which contracts later than other regions is subjected to both an increased preload and afterload. This situation is created frequently by the ventricular conduction delays associated with heart failure and ventricular dysfunction due to an MI. The increased wall stress to the late-activating myocardial regions is most probably the trigger for ventricular remodeling. By pacing one or more sites in a ventricle near the infarcted region in a manner which may cause a more coordinated contraction, CRT provides pre-excitation of myocardial regions which would otherwise be activated later during systole and experience increased wall stress. The pre-excitation of the remodeled region relative to other regions unloads the region from mechanical stress and allows reversal or prevention of remodeling to occur. Cardioversion, an electrical shock delivered to the heart synchronously with the QRS complex, and defibrillation, an electrical shock delivered without synchronization to the QRS complex, can be used to terminate most tachyarrhythmias. The electric shock terminates the tachyarrhythmia by simultaneously depolarizing the myocardium and rendering it refractory. A class of CRM devices known as an implantable cardioverter defibrillator (ICD) provides this kind of therapy by delivering a shock pulse to the heart when the device detects tachyarrhythmias. Another type of electrical therapy for tachycardia is anti-tachycardia pacing (ATP). In ventricular ATP, the ventricles are competitively paced with one or more pacing pulses in an effort to interrupt the reentrant circuit causing the tachycardia. Modern ICDs typically have ATP capability, and deliver ATP therapy or a shock pulse when a tachyarrhythmia is detected.

Systems, Device and Methods

Figure 2:
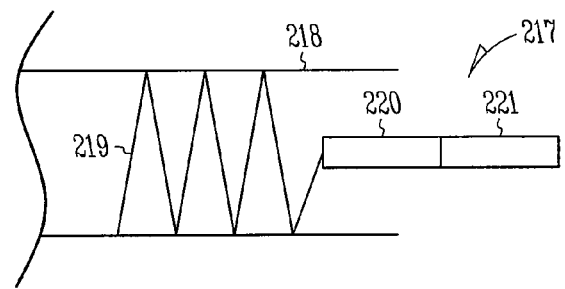
FIG. 2 illustrates an embodiment of a pulmonary artery (PA) device implanted within a pulmonary artery.

FIG. 2 illustrates an embodiment of the PA device 217 implanted within a pulmonary artery 218. The illustrated PA device includes a structure 219 that functions as both electrode(s) and an anchor for the device within the pulmonary artery, a module 220 configured to provide sensing and control functions, and a rechargeable battery 221. Some PA device embodiments provide the capability to sense PA pressure. The rechargeable battery is rechargeable using a wireless means for transferring power. For example, the PA device may have the appropriate transducers to receive ultrasound or radio frequency energy, and convert that energy into electrical charge. According to some embodiments, the illustrated PA device has autonomous control of the neural stimulation therapy.

Figure 3:
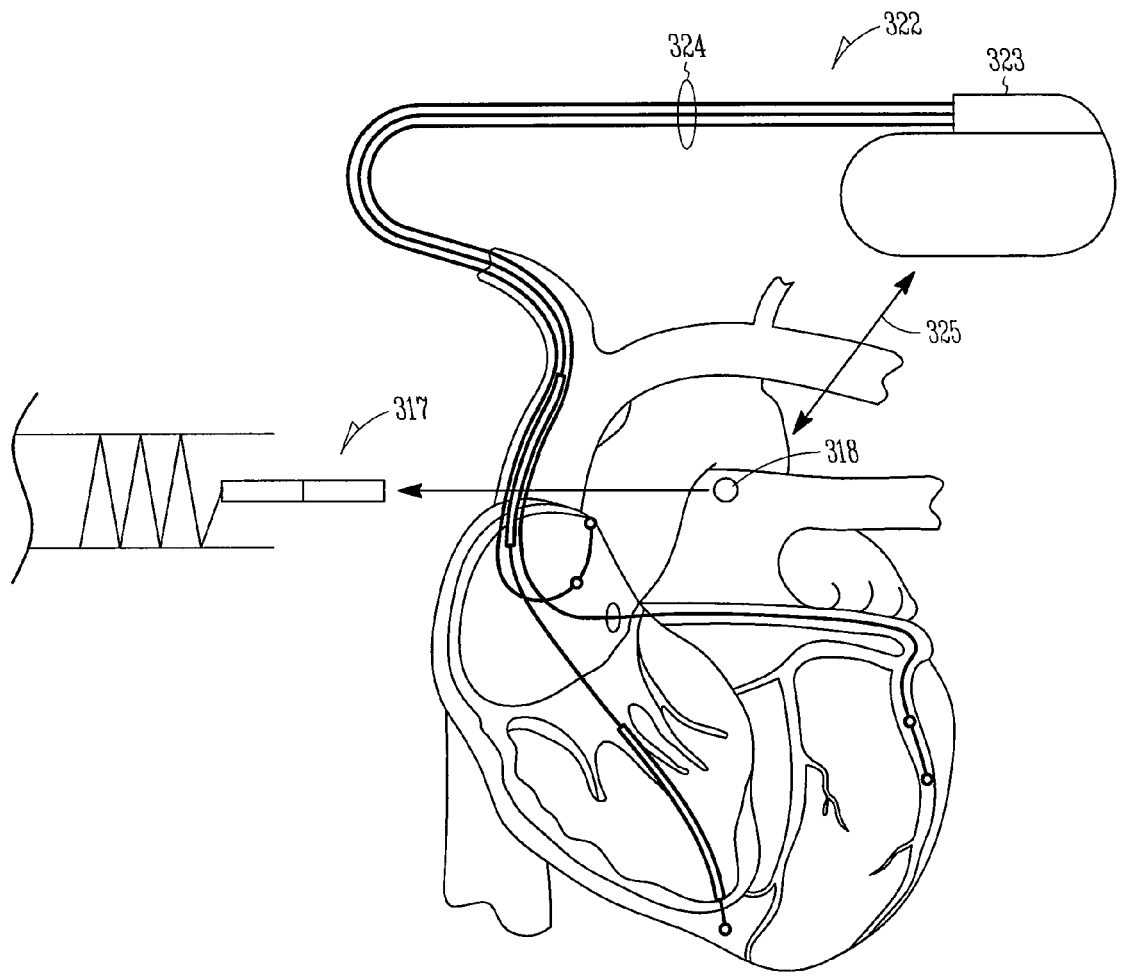
FIG. 3 illustrates a system that includes an implantable cardiac rhythm management (CRM) device and a PA device implanted in the pulmonary artery.

FIG. 3 illustrates a system that includes an implantable CRM device 322 and a PA device 317 implanted in the pulmonary artery 318. The illustrated CRM device includes a can 323, and associated CRM leads 324 with the appropriate electrodes used to sense and stimulate the myocardium. As illustrated by the arrow 325, the PA device 317 and can 323 are able to wirelessly communicate. Thus, in the illustrated embodiment, at least some of the neural stimulation control for the PA device 317 can be performed within the can 323 of the CRM device. Also, various sensed parameters (e.g. heart rate, respiration, ECG measurements, impedance) and/or detected events (e.g. arrhythmia, myocardial infarction) can function as inputs for the neural stimulation therapy performed using the PA device.

According to some embodiments, the PA device is anchored in the pulmonary artery using an expandable balloon that allows for substantially unobstructed flow of blood when inflated. Examples of non-obstructive balloons are illustrated in application Ser. No. 11/748,171, filed May 14, 2007, entitled Method and Apparatus for Regulating Blood Volume Using Volume Receptor Stimulation, which is herein incorporated by reference in its entirety.

Figure 4:
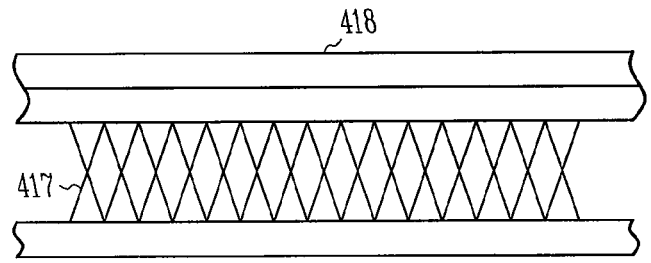
FIGS. 4-8 illustrates some PA device embodiments.
Figure 5:
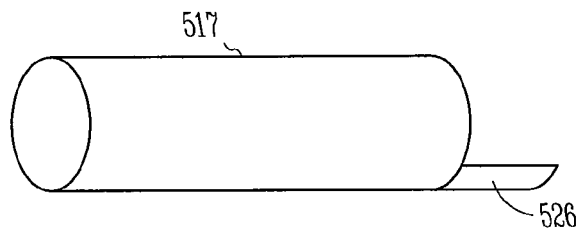
Figure 6:
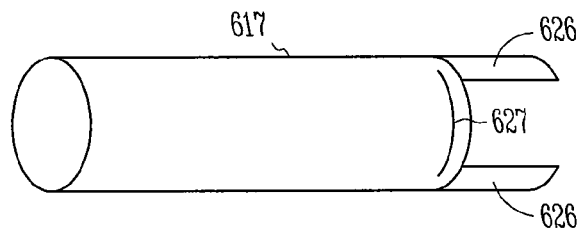

FIGS. 4-8 illustrates some PA device embodiments. FIG. 4 illustrates a chronically-implanted, PA device 417 in the form of a stent placed within the pulmonary artery 418 in which the device includes an encapsulated electronics platform. Intelligent functions, in addition to the mechanical function of preventing restenosis, are capable of being performed by the stent because of circuitry, or Microsystems, contained on the electronics platform. The chronically-implanted device diminishes problems associated with invasive surgical procedures because the device is small and is capable of being placed by a catheter, for example, into position through the vascular network of a biosystem. FIG. 5 illustrates one embodiment of a chronically-implanted PA device 517 in the form of a stent that includes an encapsulated electronics platform 526. FIG. 6 illustrates one embodiment of a chronically-implanted PA device 617 in the form of a stent that includes two encapsulated electronics platforms 626. Additional electronic platforms may be incorporated as desired. One embodiment of the device includes at least one dedicated electrical connector that couples two or more electronics platforms. One embodiment of the device uses an insulated strand of mesh 627 from the stent structure to couple two or more electronics platforms.

Figure 7:
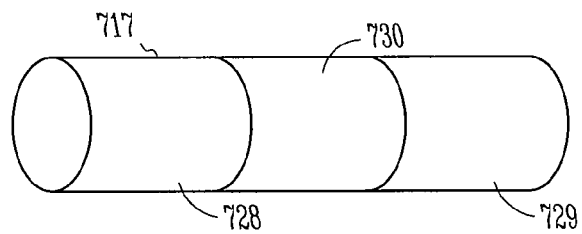
Figure 8:
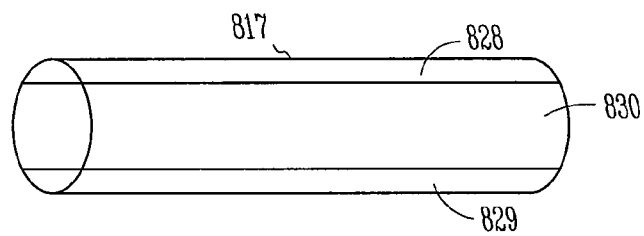

The stent-like structure of one embodiment of a chronically-implanted device includes at least two conducting portions separated by an insulator. One of the conducting portions functions as an anode and another functions as a cathode. These conducting portions are used, according to various embodiments of the chronically-implanted device, to provide electrical therapy (e.g. neural stimulation), to receive power transmissions, and/or to receive and transmit communication transmissions. FIG. 7 illustrates one embodiment of a chronically-implanted PA device 717 having a cylindrical or radially-oriented anode 728 and cathode 729. FIG. 8 illustrates one embodiment of a chronically-implanted device 817 having a longitudinally-oriented anode 828 and cathode 829. According to various embodiments, these split stent-like structures are formed from a stent. The stent is cut as required to form or isolate a radially-oriented anode and cathode or a longitudinally-oriented anode and cathode. The anode and cathode are recombined using an insulator material 730 or 830.

Figure 9:
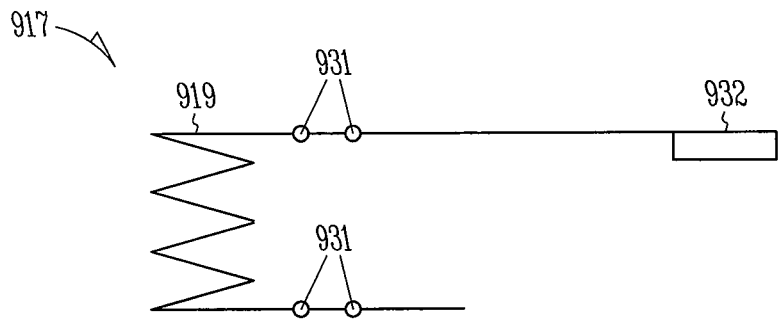
FIGS. 9-11 illustrate, for example, some variations of the PA device.
Figure 10:
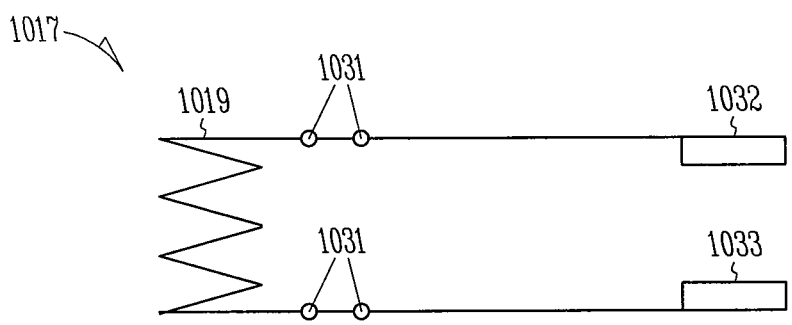
Figure 11:
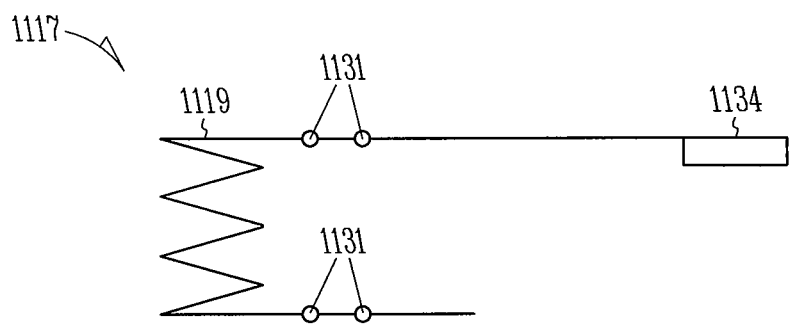

FIGS. 9-11 illustrate, for example, some variations of the PA device. FIG. 9 illustrates a PA device 917 with an anchor 919, electrodes 931 built on the anchor, and a module 932 configured to sense PA pressure and control the neural stimulation (e.g. baroreceptor stimulation) using the electrodes 931. FIG. 10 illustrates a PA device 1017 with an anchor 1019, electrodes 1031 built on the anchor, a pulmonary artery pressure sensor 1032 and related circuitry, and a separate module 1033 configured to control the pacing and sensing function. FIG. 11 illustrates a PA device 1117 with an anchor 1119, electrodes 1131 built on the anchor, and a module 1134 configured to control pacing and to receive sensing information from another device internal to the pulmonary artery or external to the pulmonary artery.

FIG. 12A-12D illustrate various embodiments of PA devices to position electrode(s) in left and/or right pulmonary arteries. Various numbers of electrodes can be positioned within each pulmonary artery. Additionally, various types of electrodes can be used, including tip and ring electrodes on a tether extending from the PA device, coil electrodes such as can be used for defibrillation shocks in embodiments that provide antitachycardia functions, and expandable stent-like electrodes. Some devices are configured to provide bipolar stimulation (e.g. stimulation vector between ring and electrode) and some devices are configured to provide unipolar stimulation (e.g. stimulation vector between electrode on lead and another electrode on another lead or a conductive housing). Various PA device embodiments are preformed to appropriately abut against a wall of the pulmonary artery and passively fixate the lead therein. Active fixation may also be used.

Figure 12A:
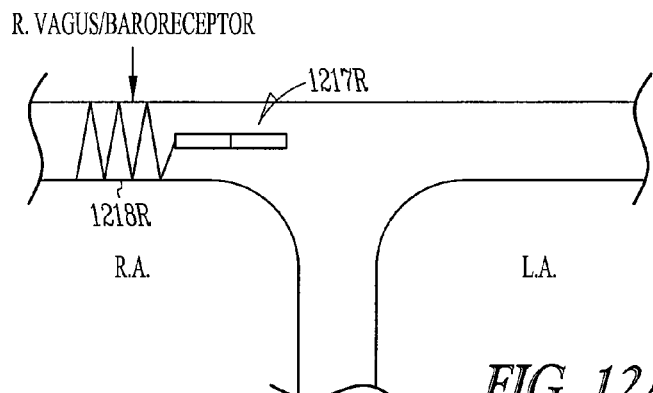
FIG. 12A-12D illustrate various embodiments of PA devices to position electrode(s) in left and/or right pulmonary arteries.
Figure 12B:
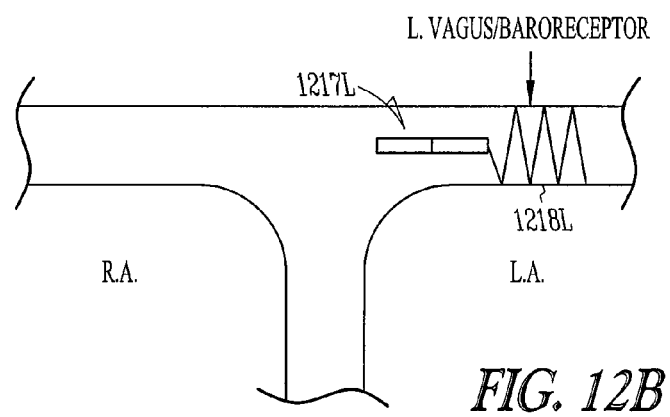

FIG. 12A illustrates a PA device 1217R adapted to be fed through the pulmonary valve and into the right pulmonary artery 1218R. In some embodiments, at least one of the electrodes is configured and positioned to elicit depolarization of the right vagus nerve; and in some embodiments, at least one of the electrodes is configured and positioned to capture baroreceptors in the right pulmonary artery. FIG. 12B illustrates a PA device 1217L adapted to be fed through the pulmonary valve and into the left pulmonary artery 2118L. In some embodiments, at least one of the electrodes is configured and positioned to elicit depolarization of the left vagus nerve; and in at least some embodiments, at least one of the electrodes is configured and positioned to capture baroreceptors in the left pulmonary artery.

Various embodiments target baroreceptors in the right and/or left pulmonary arteries. Various embodiments target the right vagal branch, the left vagal branch or a combination of the right and left vagal branches. The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart.

Figure 12C:
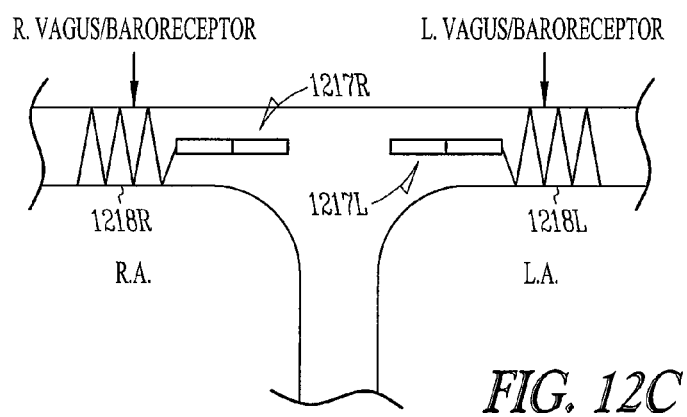
Figure 12D:
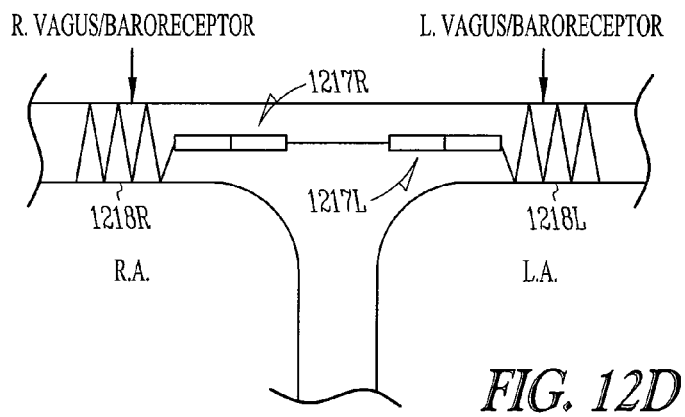

FIGS. 12C and 12D illustrates a first PA device 1217R adapted to be fed through a pulmonary valve and secured within a right pulmonary artery 1218R, and a second PA device 1217L adapted to be fed through a pulmonary valve and secured within a left pulmonary artery 1218L. The devices are operational without a wire connection extending through the pulmonary valve. The devices in FIG. 12C communicate wirelessly with each other. Sensing and therapy information can be shared between the devices. Some embodiments use one device for electrical therapy, and the other device for sensing. As illustrated in FIG. 12D, the devices communicate with each through a wired connection (e.g. tether extending between the devices).

Figure 13:
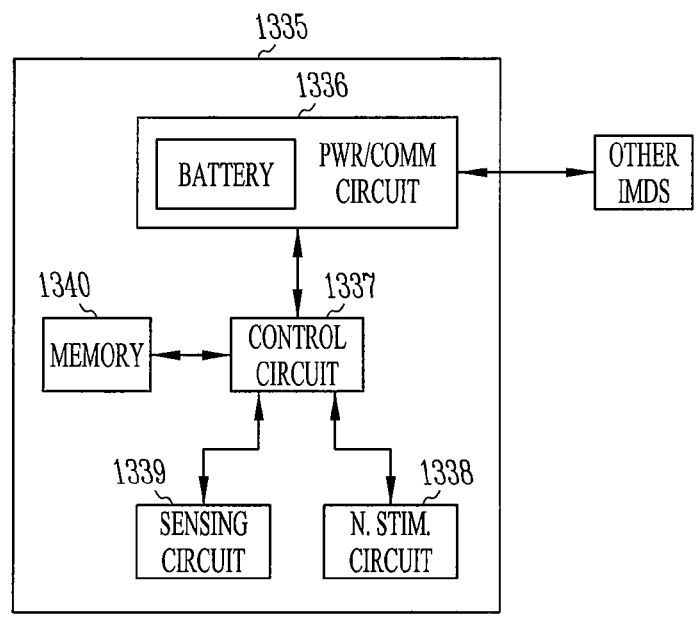
FIG. 13 is a block diagram of one embodiment of a chronically-implanted PA device.

FIG. 13 is a block diagram of one embodiment of a chronically-implanted PA device 1335. According to the illustrated embodiment, the device 1335 includes a power/communication circuit 1336, a control circuit 1337, a neural stimulation circuit 1338, and a sensing circuit 1339. The neural stimulation circuit functions as a therapy-providing circuit which is operative to provide the desired therapy, such as neural stimulation therapy to treat hypertension, ischemia, heart failure, or arrhythmias. In an embodiment, the sensing circuit is operative to sense PA pressure, and in some embodiment sense heart rate or derive heart rate from the sensed PA pressure.

The illustrated power and communication circuitry 1336 includes a rechargeable battery, which is capable of being recharged using ultrasound signals or using other wireless power transfer technology. The power and communication circuitry 1336 are combined into one box to illustrate that they are capable of being integrated. The controller monitors, controls, or monitors and controls the functions of any or all of the components. According to various embodiments, the controller is adapted to trigger the sensing circuit, the stimulating circuit, or the sensing and stimulating circuits. According to one embodiment, the controller is used to manage system power by controlling power flow between the power circuitry and other system components. The controller is capable of controlling the operation of any system component, and of providing the system clock for electronics timing and functionality. The controller can be a state machine. The illustrated device includes a memory 1340, which can store instructions and sensed data. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The neural stimulation circuitry is used to apply electrical stimulation pulses to desired neural target sites, such as baroreceptor sites in the pulmonary artery, through one or more stimulation electrodes. In various embodiments, at least one electrode is connected to the neural stimulation circuitry using a tether such that the neural stimulation circuitry applies electrical stimulation through the tether and electrode. In various embodiments, at least one electrode is integrated with or otherwise formed on the housing of the device (or a stent-like or balloon-like anchor structure) such that the neural stimulation circuitry applies electrical stimulation through the electrode on the housing. The sensor circuitry can be used to provide feedback for the neural stimulation. For example, the sensing circuit can be used to detect and process ANS nerve activity, blood pressure, or heart rate. According to various embodiments, the stimulation circuitry includes modules to set any one or any combination of two or more of the following pulse features: the amplitude of the stimulation pulse, the frequency of the stimulation pulse, the duty cycle of the pulse, the duration of each period of neural stimulation therapy, the duration of the neural stimulation pulse train, and the wave morphology of the pulse. Examples of wave morphology include a square wave, triangle wave, sinusoidal wave, and waves with desired harmonic components to mimic white noise such as is indicative of naturally-occurring baroreflex stimulation.

Various PA device embodiments include a pressure sensor to monitor changes in blood pressure in the pulmonary artery. Thus, the sensor monitors the effect of the neural stimulation. In various embodiments, for example, MEMS technology is used to sense the blood pressure. Some sensor embodiments determine blood pressure based on a displacement of a membrane. The stimulator and sensor functions can be integrated, even if the stimulator and sensors are located in separate devices.

Examples of pressure sensors include capacitive membrane and piezoelectric sensors. According to various embodiments, the capacitive membrane sensor is used to measure pressure, to derive flow, to derive rate, to monitor cardiac output, to monitor hemodynamic stability, and to monitor Electro-Mechanical Dissociation (EMD). There is a correlation between cardiac electrical abnormalities and coronary vascular abnormalities. However, it is possible that the electrical functions appear normal but the mechanical functions are abnormal, or that the mechanical functions are normal but the electrical functions appear abnormal. EMD identifies conditions in which electrical and mechanical functions of the biological system are not in accord or agreement with each other.

Thus, various embodiments of the present subject matter provide a PA device that automatically modulates neural stimulation to the PA baroreceptors based, at least in part, on localized feedback from the pressure sensor in the pulmonary artery. This localized sensing improves feedback control. According to various embodiments, the device monitors pulmonary pressure parameters such as mean, systolic, diastolic pressure and the like. As mean pulmonary pressure increases or remains above a programmable target pressure, for example, the device stimulates the baroreflex at an increased rate to reduce blood pressure and control hypertension. As mean pulmonary pressure decreases towards the target pressure, the device responds by reducing the stimulation of the baroreflex. In various embodiments, the algorithm takes into account the current metabolic state (cardiac demand) and adjusts neural stimulation accordingly.

According to one embodiment, the sensor functions provided by the device are capable of providing continuous intravascular measurements, such as blood pressure, blood flow and vessel size. According to various embodiments, the sensor is used to measure pressure, and can be used to derive flow, to derive rate, to monitor cardiac output, to monitor hemodynamic stability, to monitor EMD and to measure contraction strength of the heart.

Figure 14:
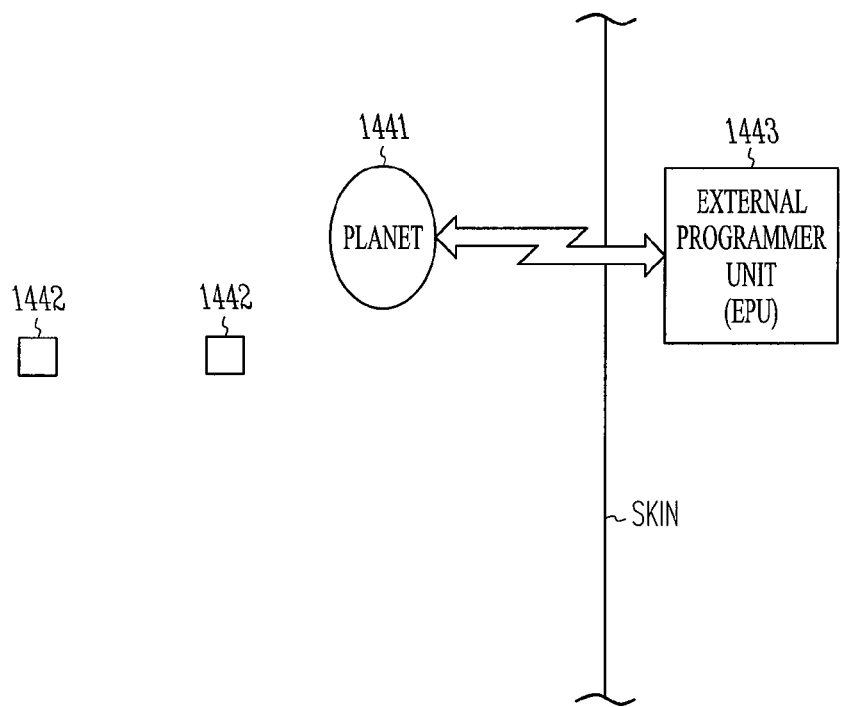
FIG. 14 illustrates a network including an implantable planet and satellite PA devices, illustrated as a left PA device and a right PA device.

The PA device can be incorporated as a satellite in a satellite-planet configuration. FIG. 14 illustrates a network including an implantable planet 1441 and satellite PA devices 1442, illustrated as a left PA device and a right PA device. The planet is capable of wirelessly communicating, i.e. without a direct electrical connection, to each satellite using telemetry, for example. The planet individually commands each satellite to provide sensing functions and/or therapy functions. The satellites can function autonomously and communicate with the planet. This communication is initiated by the planet and/or by the satellite in various embodiments. In the illustrated embodiment, a programmer 1443 wirelessly communicates with the planet, which in turn wirelessly communicates with the satellites. In some embodiments, the programmer is able to wirelessly communicate directly with at least one satellite. Some embodiments are adapted to inductively communicate.

Figure 15:
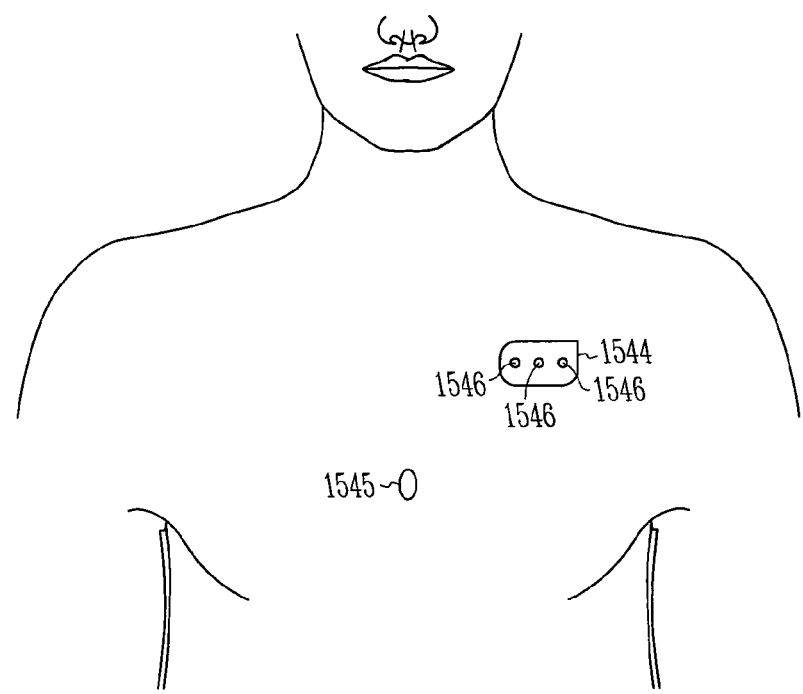
FIG. 15 illustrates a system including an implantable medical device (IMD) and a PA device, according to various embodiments.

FIG. 15 illustrates a system including an IMD 1544 and a PA device 1545, according to various embodiments. Various embodiments of the IMD 1544 include NS functions only, and various embodiments include a combination of NS and CRM functions. The IMD 1544 and PA device 1545 are capable of wirelessly communicating data and instructions. According to various embodiments, the IMD 1544 stimulates baroreceptors in the pulmonary artery using the PA device 1545 positioned in the pulmonary artery. In the illustrated example, the IMD includes wireless ECG electrodes 1546 (not necessarily arranged as illustrated), which can be used to detect cardiac signals.

Figure 16:
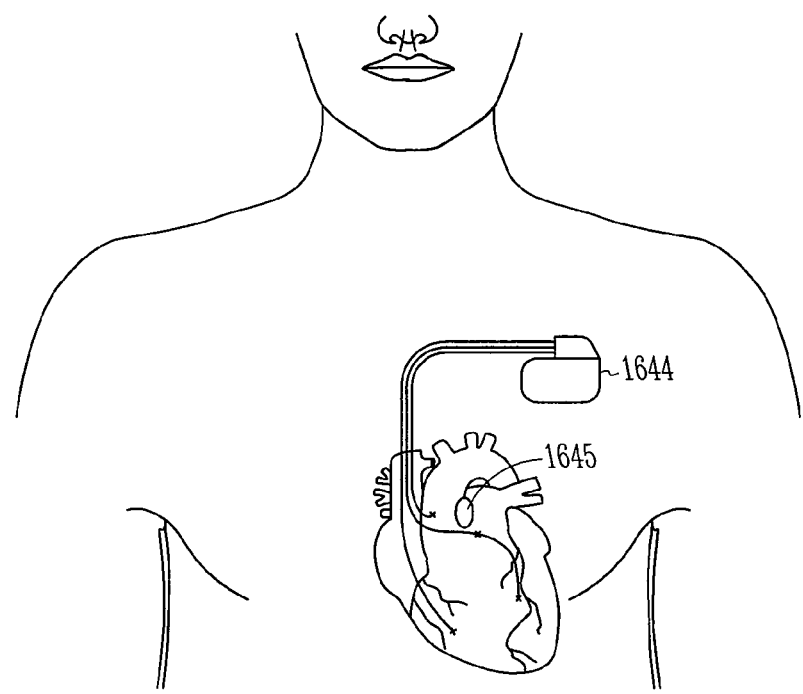
FIG. 16 illustrates a system including an implantable CRM device and a PA device, according to various embodiments.

FIG. 16 illustrates a system including an implantable CRM device 1644 and a PA device 1645, according to various embodiments. Communication can be between a PA device and a CRM device. In various embodiments, this communication allows one of the devices to deliver more appropriate therapy (i.e. more appropriate neural stimulation therapy or CRM therapy) based on data received from the other device. Some embodiments provide on-demand communications. The illustrated PA device and the CRM device are capable of wirelessly communicating with each other. A programmer is capable of wirelessly communicating with at least one of the NS and the CRM devices. For example, various embodiments use telemetry coils to wirelessly communicate data and instructions to each other. In other embodiments, communication of data and/or energy is by ultrasonic means. PA device(s) is (are) capable of being used to transvascularly stimulate targeted parasympathetic nerves anatomically located proximate to the left and right pulmonary artery at a strength sufficient to stimulate PA baroreceptors and/or to elicit depolarization of adjacent autonomic nerves, and is (are) also capable of being used to deliver left and right atrial pacing pulses, for example. Such atrial pacing can be provided in some CRT applications.

According to various embodiments, the device is designed to sense a refractory period, and to deliver the neural stimulation from an electrode or electrodes within the pulmonary artery during the refractory period to avoid unintentionally capturing cardiac tissue and inducing an arrhythmia such as atrial or ventricular fibrillation. The myelinated vagal nerve fibers of a parasympathetic nervous system is much lower than that of myocardial tissue. Thus, when stimulating these myelinated vagal nerve fibers, parasympathetic stimulation can be applied in the absence of myocardial stimulation.

Figure 17:
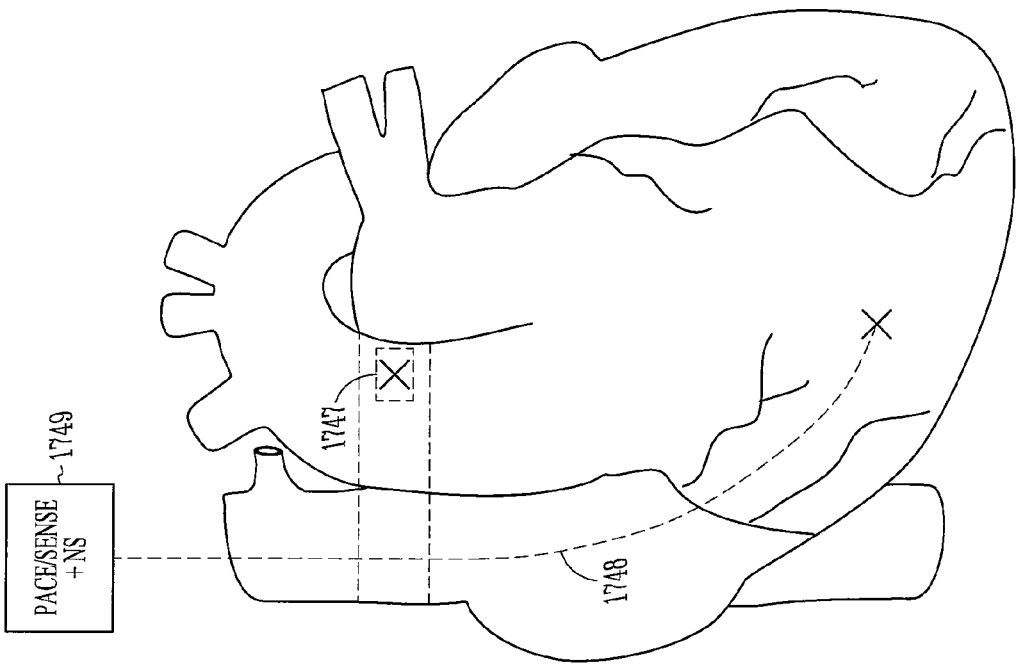
FIG. 17 illustrates an embodiment with a right PA device and a right ventricle lead.

FIG. 17 illustrates an embodiment with a right PA device 1747 and a right ventricle lead 1748. The illustrated IMD 1749 wirelessly communicates with the right PA device 1747, and is capable of performing right atrial pacing and sensing and controlling neural stimulation of pulmonary artery baroreceptor and/or a right vagus nerve target using electrode(s) on the right PA device 1747. In some embodiments, atrial events can be sensed from the same electrode(s) on the right PA device. Neural stimulation can be synchronized with sensed p-waves to avoid unintentionally capturing the right atrium during the neural stimulation. Some right PA device embodiments use electrode(s) specifically configured and positioned to stimulate pulmonary artery baroreceptors and/or a neural target of the right vagus nerve and to use electrode(s) specifically configured and positioned to capture right atrial tissue. Some embodiments control signal parameters, such as amplitude and frequency, of the stimulation signal to control whether the stimulation signal depolarizes a neural pathway and/or captures atrial tissue. An application for the illustrated IMD includes vagal modulation with the ability to synchronize the vagal modulation to refractory periods associated with paced or intrinsic atrial events to avoid unintentional atrial capture caused by the vagal modulation.

Figure 18:
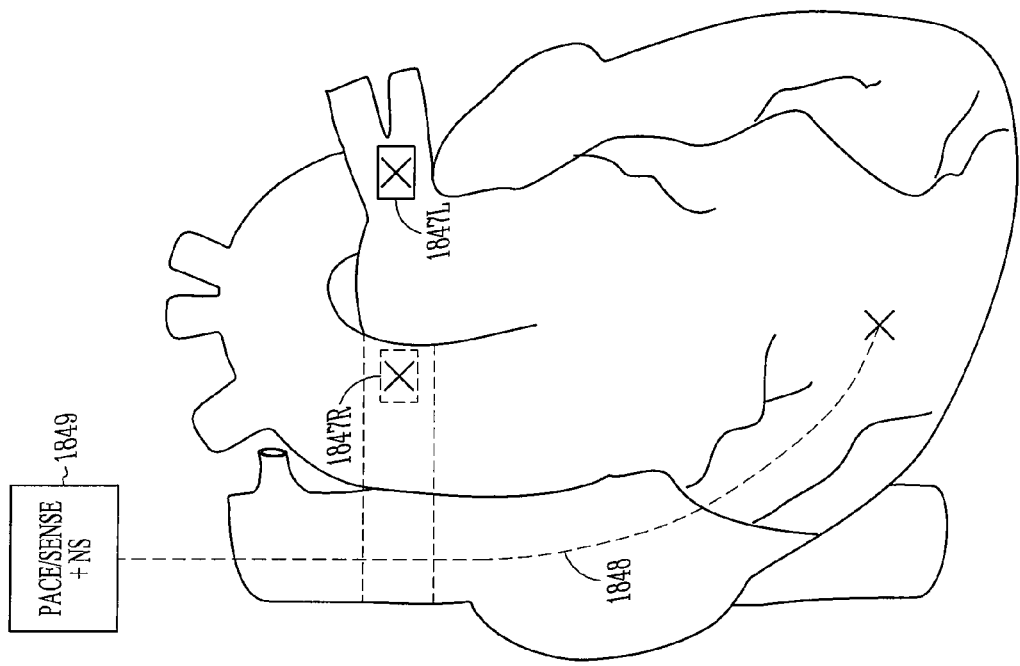
FIG. 18 illustrates an embodiment with a right PA device and a left PA device, and with a right ventricle lead.

FIG. 18 illustrates an embodiment with a right PA device 1847R and a left PA device 1847L, and with a right ventricle lead 1848. The illustrated IMD 1849 wirelessly communicates with the PA devices to control neural stimulation (e.g. baroreceptors stimulation). In some embodiments, the illustrated IMD 1849 is capable of performing biatrial pacing using the PA devices. In addition to stimulating neural targets (baroreceptors or a branch of the vagus) from the pulmonary artery, some PA device embodiments are also capable of sensing atrial events using electrode(s) in the right and/or left pulmonary arteries, and/or pacing or defibrillating atrial tissue using electrode(s) in the right and/or left pulmonary arteries. Atrial events can be sensed from the same electrode(s). Neural stimulation can be timed based on sensed p-waves to avoid unintentionally capturing atrial tissue. Some embodiments use electrode(s) specifically configured and positioned to stimulate a neural target and electrode(s) specifically configured and positioned to capture atrial tissue. Some embodiments control signal parameters, such as amplitude and frequency, of the stimulation signal to control whether the stimulation signal depolarizes a neural pathway and/or captures atrial tissue.

Figure 19:
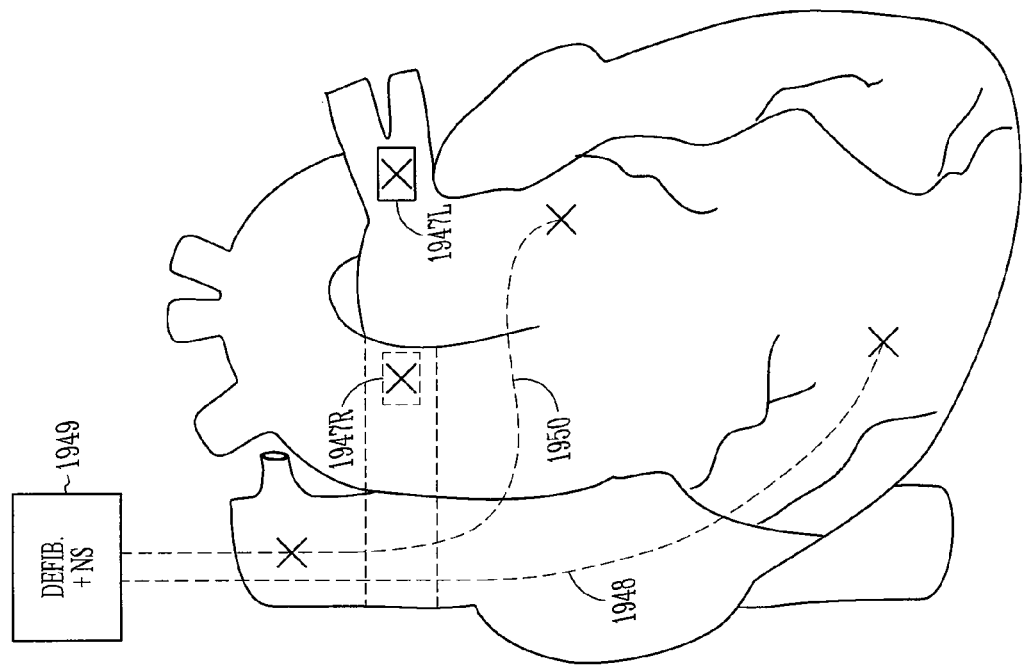
FIG. 19 illustrates an embodiment capable of providing atrial defibrillation therapy integrated with vagal stimulation.

FIG. 19 illustrates an embodiment capable of providing atrial defibrillation therapy integrated with vagal stimulation. The illustrated system includes a right ventricle lead 1948, and a coronary sinus lead 1950, a right PA device 1947R and a left PA device 1947L. The illustrated IMD 1949 is capable of providing an atrial shock using a variety of configurations, and is also capable of stimulating neural targets, such as pulmonary artery baroreceptors, from within the pulmonary artery. Potential benefits of stimulating vagal cardiac nerves include reducing inflammatory response following myocardial infarction, and reducing the electrical stimulation threshold for defibrillating. For example, when a tachycardia is sensed, vagal nerve stimulation is applied, and then a defibrillation shock is applied. The vagal nerve stimulation allows the defibrillation shock to be applied at less energy. The illustrated right ventricle lead 1948 is an endocardial bi-polar lead with electrodes arranged for establishing electrical contact with the right ventricle of the heart. These electrodes permit bi-polar sensing of ventricular activations in the right ventricle. The illustrated lead 1948 is fed through the superior vena cava, into the right atrium and then into the right ventricle. The illustrated coronary sinus lead 1950 is an atrial shocking lead, generally including a first or tip electrode and a second or proximal electrode. Additional electrodes can be incorporated on the lead 1950. Such electrodes may be useful in placing the lead by providing various potential electrode configurations for use in providing the desired sensing and stimulating functions. The coronary sinus lead 1950 is flexible and arranged to be passed down the superior vena cava, into the right atrium, into the coronary sinus ostium, and advanced into the coronary sinus channel of the heart near the left side thereof so that the first or tip electrode is within the coronary sinus channel either within the coronary sinus adjacent the left ventricle and beneath the left atrium or within the great cardiac vein adjacent the left ventricle and beneath the left atrium. The electrodes are spaced apart such that when the first electrode is positioned as described above, the second electrode is in the right atrium. The electrodes on the coronary sinus lead 1950 are capable of providing bi-polar sensing of heart activity in the atria, and further are capable of delivering defibrillating or cardioverting electrical energy to the atria. Defibrillating energy can also be applied between the can or housing of the IMD 1949 and other electrode(s) on the right ventricle lead 1948 and the coronary sinus lead 1950. The PA devices 1947R and 1947L can be used with the coronary sinus lead 1950 and right ventricle lead 1948. The electrodes of the PA devices can be positioned and configured to provide targeted stimulation of pulmonary artery baroreceptors and/or a particular vagal pathway, to be used in sensing left and/or right atrial activity, and/or to be used to capture right and/or left atrial tissue. The electrodes on the PA devices 1947R and 1947L can be used with a conductive housing on the IMD 1949 or with other electrodes on other leads, such as the coronary sinus lead 1950, to provide desired sensing, pacing and shocking vectors. The PA devices can be used independent of the coronary sinus lead and right ventricle lead. Electrodes on the PA devices can provide vagal stimulation, along appropriate sensing, pacing and shocking vectors using other electrodes.

Figure 20:
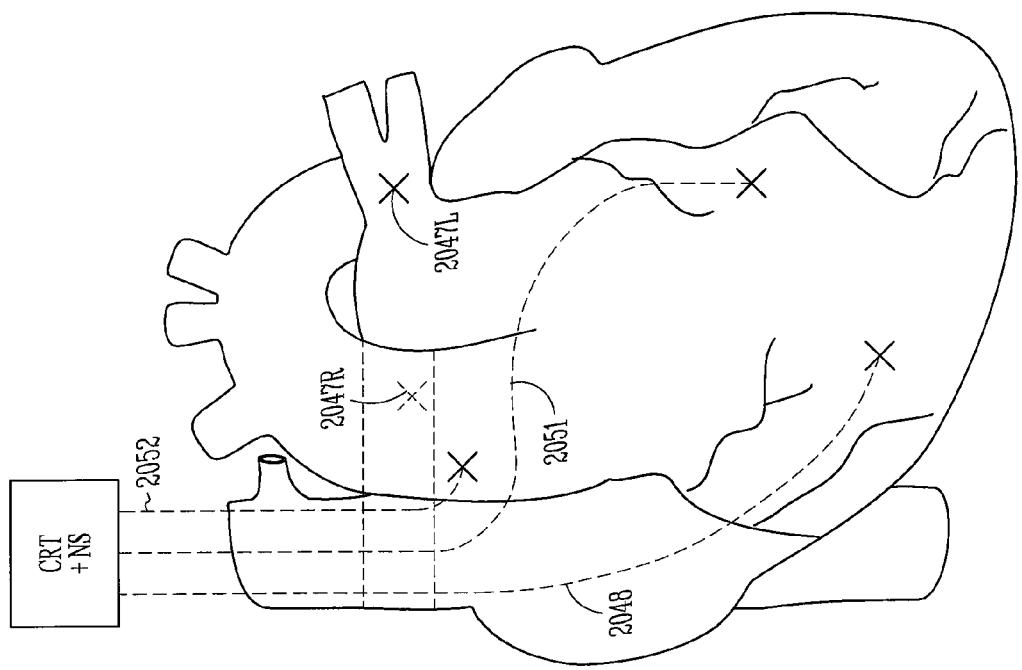
FIG. 20 illustrates an embodiment capable of providing cardiac resynchronization therapy (CRT) integrated with vagal stimulation.

FIG. 20 illustrates an embodiment capable of providing CRT integrated with vagal stimulation. The illustrated embodiment includes a left ventricle lead 2051 extending through the coronary sinus, a right ventricle lead 2048, and a right atrial lead 2052. The illustrated system also includes a left PA device 2047L and a right PA device 2047R. The illustrated left ventricle lead 2051 is fed through the coronary sinus and further advanced into branch veins. Various embodiments of the illustrated device are capable of providing vagal stimulation along with biventricular pacing and/or biatrial pacing to provide resynchronization therapy. Some embodiments provide biatrial pacing using electrodes in the right and left pulmonary arteries. The synchronization provided by biatrial pacing can reduce an atrial tachycardia and atrial fibrillation burden, such as a reentry tachycardia.

Figure 21:
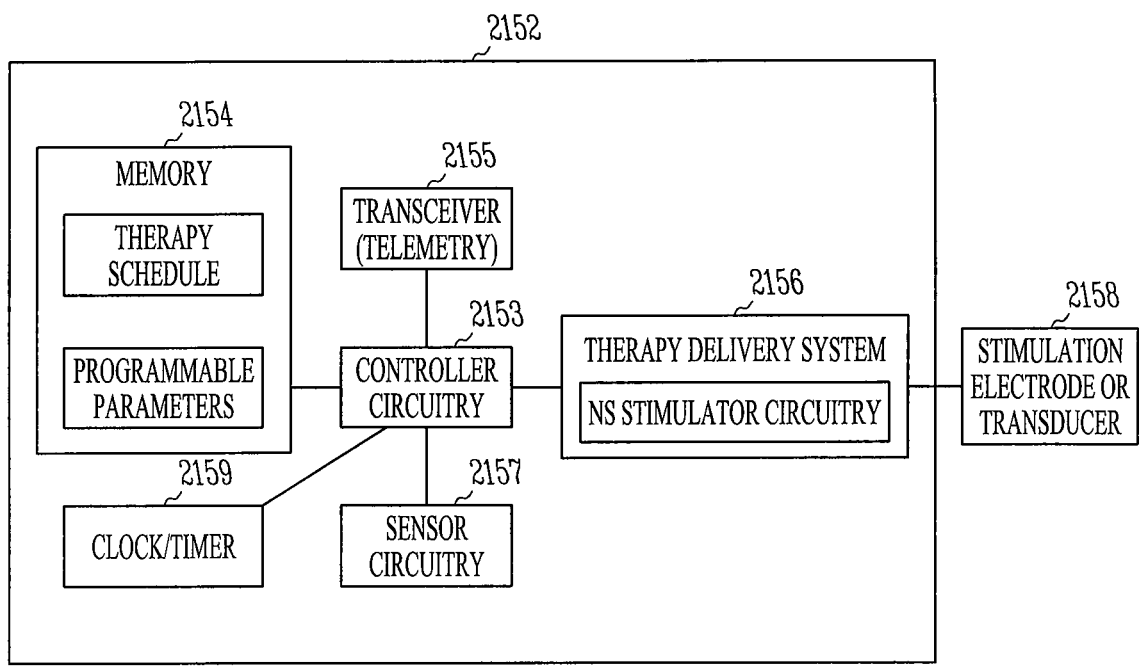
FIG. 21 illustrates a PA device, according to various embodiments.

FIG. 21 illustrates a PA device 2152, according to various embodiments. The illustrated device provides neural stimulation signals for delivery to predetermined neural targets (pulmonary artery baroreceptors and/or vagal branches that pass proximate to the pulmonary artery) to provide a therapy using an elicited neural stimulation response. The illustrated device includes controller circuitry 2153 and memory 2154. The controller circuitry is capable of being implemented using hardware, software, and combinations of hardware and software. For example, according to various embodiments, the controller circuitry includes a processor to perform instructions embedded in the memory to perform functions associated with the neural stimulation therapy. The illustrated device further includes a transceiver 2155 and associated circuitry for use to communicate with a programmer or another external or internal device. Various embodiments have wireless communication capabilities. For example, some transceiver embodiments use a telemetry coil to wirelessly communicate with a programmer or another external or internal device.

The illustrated device further includes a therapy delivery system 2156, such as neural stimulation circuitry to stimulate baroreceptors and elicit a baroreflex response. The illustrated device also includes sensor circuitry 2157. The sensor circuitry can be used to detect parameter(s) useful to determine a cardiac condition or provide feedback for a therapy. Some embodiments use sensor circuitry adapted to detect nerve traffic. Other physiological parameters, such as heart rate, respiration, and blood pressure can be sensed. A PA device embodiment includes a PA pressure sensor. According to various embodiments, the neural stimulation circuitry is used to apply electrical stimulation pulses to desired neural targets, such as through one or more stimulation electrodes 2158 positioned at predetermined location(s). Some embodiments use transducers to provide other types of energy, such as ultrasound, light or magnetic energy. The controller circuitry can control the therapy using a therapy schedule in memory, or can compare a target range (or ranges) of the sensed physiological response(s) stored in the memory to the sensed physiological response(s) to appropriately adjust the intensity of the neural stimulation/inhibition. The target range(s) can be programmable.

According to various embodiments using neural stimulation, the stimulation circuitry is adapted to set or adjust any one or any combination of stimulation features. The intensity of a neural stimulation therapy can be adjusted by adjusting one or more stimulation features. Examples of stimulation features include the amplitude, frequency, polarity and wave morphology of the stimulation signal. Examples of wave morphology include a square wave, triangle wave, sinusoidal wave, and waves with desired harmonic components. Some embodiments of the neural stimulation circuitry are adapted to generate a stimulation signal with a predetermined amplitude, morphology, pulse width and polarity, and are further adapted to respond to a control signal from the controller to modify at least one of the amplitude, wave morphology, pulse width and polarity. Some embodiments of the neural stimulation circuitry are adapted to generate a stimulation signal with a predetermined frequency, and are further adapted to respond to a control signal from the controller to modify the frequency of the stimulation signal.

The controller can be programmed to control the neural stimulation delivered by the stimulation circuitry according to stimulation instructions, such as a stimulation schedule, stored in the memory. Neural stimulation can be delivered in a stimulation burst, which is a train of stimulation pulses at a predetermined frequency. Stimulation bursts can be characterized by burst durations and burst intervals. A burst duration is the length of time that a burst lasts. A burst interval can be identified by the time between the start of successive bursts. A programmed pattern of bursts can include any combination of burst durations and burst intervals. A simple burst pattern with one burst duration and burst interval can continue periodically for a programmed period or can follow a more complicated schedule. The programmed pattern of bursts can be more complicated, composed of multiple burst durations and burst interval sequences. The programmed pattern of bursts can be characterized by a duty cycle, which refers to a repeating cycle of neural stimulation ON for a fixed time and neural stimulation OFF for a fixed time.

According to some embodiments, the controller controls the neural stimulation generated by the stimulation circuitry by initiating each pulse of the stimulation signal. In some embodiments, the controller circuitry initiates a stimulation signal pulse train, where the stimulation signal responds to a command from the controller circuitry by generating a train of pulses at a predetermined frequency and burst duration. The predetermined frequency and burst duration of the pulse train can be programmable. The pattern of pulses in the pulse train can be a simple burst pattern with one burst duration and burst interval or can follow a more complicated burst pattern with multiple burst durations and burst intervals. In some embodiments, the controller controls the stimulation circuitry to initiate a neural stimulation session and to terminate the neural stimulation session. The burst duration of the neural stimulation session under the control of the controller can be programmable. The controller may also terminate a neural stimulation session in response to an interrupt signal, such as may be generated by one or more sensed parameters or any other condition where it is determined to be desirable to stop neural stimulation.

The illustrated device includes a clock or timer 2159 which can be used to execute the programmable stimulation schedule. Chronic neural stimulation therapies, such as for a heart failure therapy, can be programmed to occur at a particular time (e.g. night). For example, if a pathological condition and its severity are such that therapy can wait until a more convenient time for the patient, the device can be programmed to enable a therapy for the pathological condition when the pathological condition is detected and to deliver the therapy according to a programmed schedule (e.g. a particular time of day) whenever the therapy is enabled. A stimulation session can begin at a first programmed time, and can end at a second programmed time. Various embodiments initiate and/or terminate a stimulation session based on a signal triggered by a user. Various embodiments use sensed data to enable and/or disable a stimulation session. Thus, for example, the clock can be used to provide an enabling condition for the therapy. By way of another example, two or more conditions may function together to enable a therapy.

According to various embodiments, the schedule refers to the time intervals or period when the neural stimulation therapy is delivered. A schedule can be defined by a start time and an end time, or a start time and a duration. Various device embodiments apply the therapy according to the programmed schedule contingent on enabling conditions in addition to a detected pathological condition indicated for a neural stimulation therapy, such as patient rest or sleep, low heart rate levels, time of day, and the like. The therapy schedule can also specify how the stimulation is delivered, such as continuously at the pulse frequency throughout the identified therapy period (e.g. 5 Hz pulse frequency for two minutes), or according to a defined duty cycle during the therapy delivery period (e.g. 10 seconds per minute at 5 Hz pulse frequency for two minutes). As illustrated by these examples, the therapy schedule is distinguishable from the duty cycle.

Figure 22:
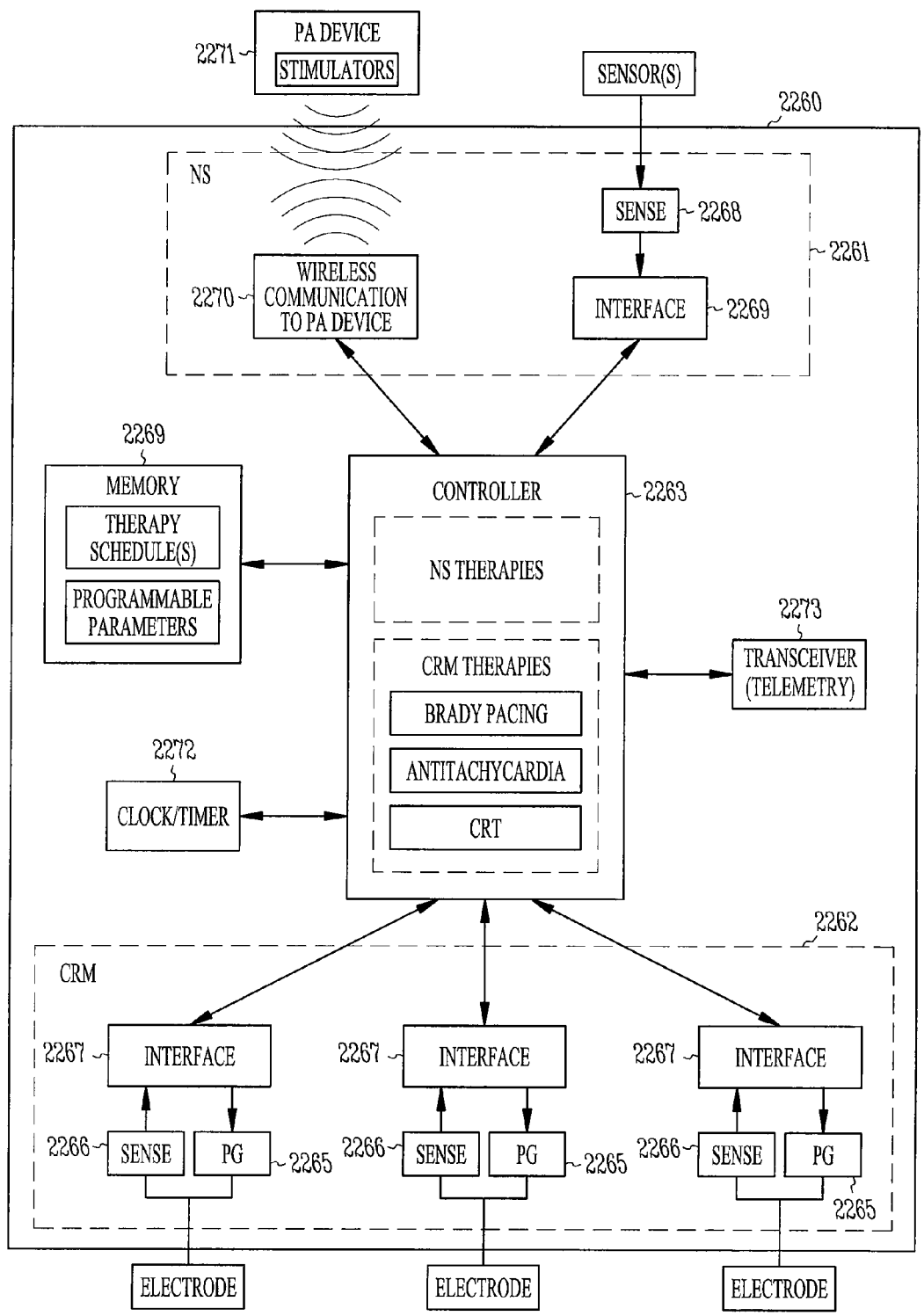
FIG. 22 illustrates an IMD having a neural stimulation (NS) component and a CRM component according to various embodiments.

FIG. 22 illustrates an IMD 2260 having a NS component 2261 and a CRM component 2262 according to various embodiments. The illustrated device includes a controller 2263 and memory 2264. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. For example, therapy schedule(s) and programmable parameters can be stored in memory. According to various embodiments, the controller includes a processor to execute instructions embedded in memory to perform the neural stimulation and CRM functions. The illustrated neural stimulation therapy may include predetermined neural stimulation therapies determined to be appropriate for specific pathological conditions, and various combinations of the pathological conditions. For example, the predetermined neural stimulation therapies can include an appropriate therapy for hypertension, an appropriate therapy for ischemia, and an appropriate therapy for a combination of hypertension and ischemia. Various embodiments include CRM therapies, such as bradycardia pacing, anti-tachycardia therapies such as ATP, defibrillation and cardioversion, and CRT.

The CRM therapy section 2262 includes components, under the control of the controller, to stimulate a heart and/or sense cardiac signals using one or more electrodes. The illustrated CRM therapy section includes a pulse generator 2265 for use to provide an electrical signal through an electrode to stimulate a heart, and further includes sense circuitry 2266 to detect and process sensed cardiac signals. An interface 2267 is generally illustrated for use to communicate between the controller 2263 and the pulse generator 2265 and sense circuitry 2266. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 2261 includes components, under the control of the controller, used to control stimulation of a neural stimulation target and/or sense parameters associated with nerve activity or surrogates of nerve activity such as heart rate, blood pressure and respiration. Sense circuits 2268 are used to detect and process signals from a sensor, such as a sensor of nerve activity, heart rate, blood pressure, respiration, impedance and the like. The interfaces 2269 are generally illustrated for use to communicate between the controller 2263 and the sense circuitry 2268. The neural stimulation therapy section includes a module 2270 to wirelessly communicate to the PA device(s) 2271, which includes the stimulation circuit to deliver neural stimulation to the PA baroreceptors or other autonomic neural target accessible using the PA device. The illustrated device further includes a clock/timer 2272, which can be used to deliver the programmed therapy according to a programmed stimulation protocol and/or schedule. The illustrated device further includes a transceiver 2273 and associated circuitry for use to communicate with a programmer or another external or internal device. Various embodiments include a telemetry coil.

Figure 23:
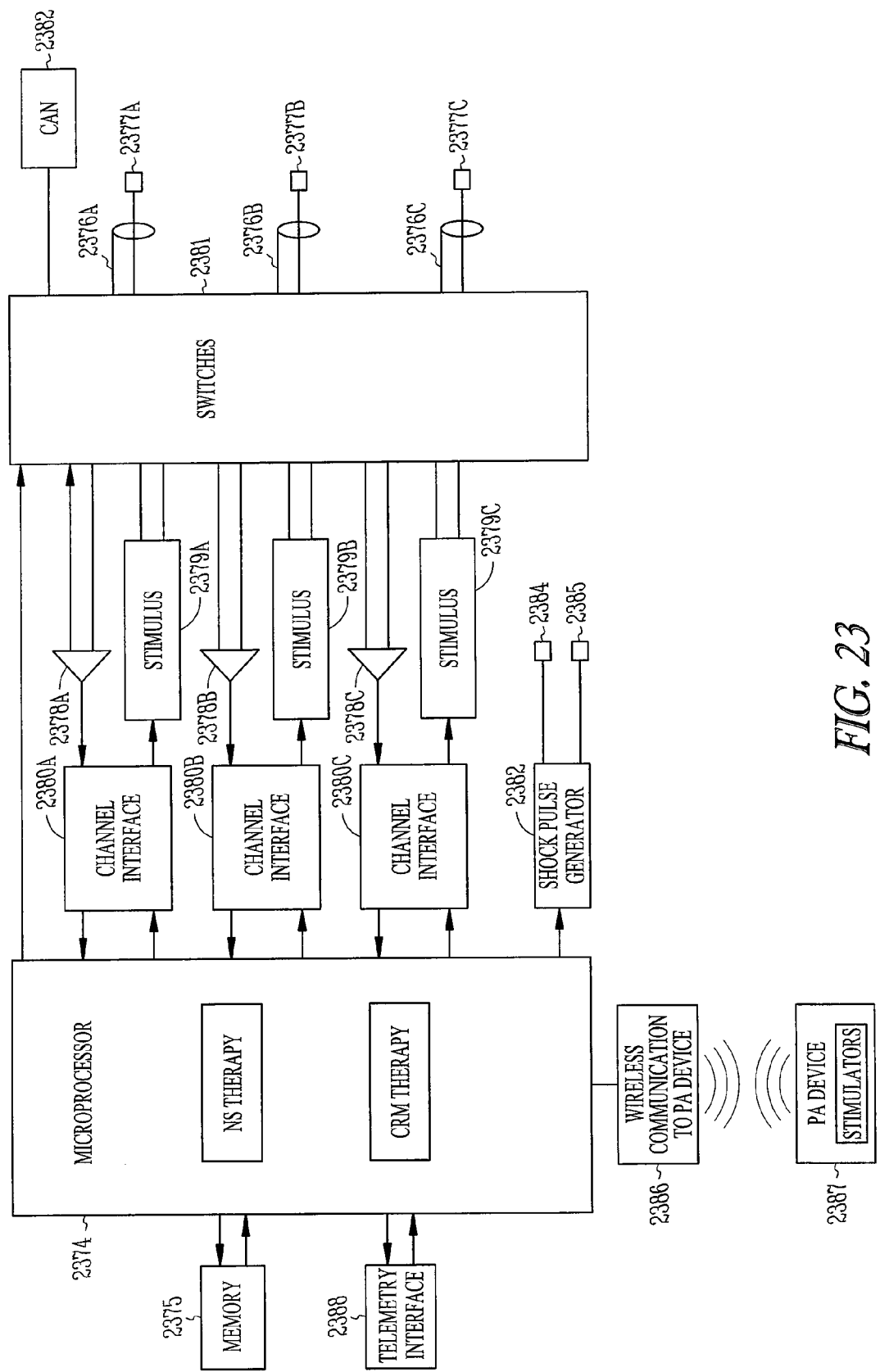
FIG. 23 shows a system diagram of an embodiment of a microprocessor-based implantable device, according to various embodiments.

FIG. 23 shows a system diagram of an embodiment of a microprocessor-based implantable device, according to various embodiments. The controller of the device is a microprocessor 2374 which communicates with a memory 2375 via a bidirectional data bus. The controller could be implemented by other types of logic circuitry (e.g., discrete components or programmable logic arrays) using a state machine type of design. As used herein, the term "circuitry" should be taken to refer to either discrete logic circuitry or to the programming of a microprocessor. Shown in the figure are three examples of sensing and pacing channels designated "A" through "C" comprising bipolar leads with ring electrodes 2376A-C and tip electrodes 2377A-C, sensing amplifiers 2378A-C, pulse generators 2379A-C, and channel interfaces 2380A-C. Each channel thus includes a pacing channel made up of the pulse generator connected to the electrode and a sensing channel made up of the sense amplifier connected to the electrode. The channel interfaces 2380A-C communicate bidirectionally with the microprocessor 2374, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing. The intrinsic atrial and/or ventricular rates can be measured by measuring the time intervals between atrial and ventricular senses, respectively, and used to detect atrial and ventricular tachyarrhythmias.

The electrodes of each bipolar lead are connected via conductors within the lead to a switching network 2381 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing (can) 2382 or an electrode on another lead serving as a ground electrode. A shock pulse generator 2383 is also interfaced to the controller for delivering a defibrillation shock via a pair of shock electrodes 2384 and 2385 upon detection of a shockable tachyarrhythmia. The illustrated device includes a module 2386 coupled to the microprocessor 2374 for wireless communication to a PA device 2387. The microprocessor controls the neural stimulation delivered by the PA device.

The figure illustrates a telemetry interface 2388 connected to the microprocessor, which can be used to communicate with an external device. The illustrated microprocessor 2377 is capable of performing neural stimulation therapy routines and myocardial (CRM) stimulation routines. Examples of NS therapy routines include hypertension, ischemia, post-MI, and heart failure remodeling therapies. Examples of myocardial therapy routines include bradycardia pacing therapies, anti-tachycardia shock therapies such as cardioversion or defibrillation therapies, ATP, and CRT.

Figure 24:
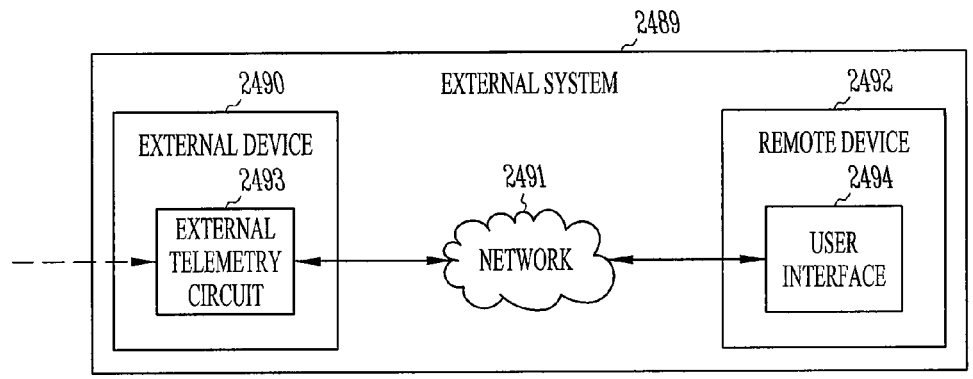
FIG. 24 is a block diagram illustrating an embodiment of an external system.

FIG. 24 is a block diagram illustrating an embodiment of an external system 2489. The external system includes a programmer, in some embodiments. In the illustrated embodiment, the external system includes a patient management system. As illustrated, the external system is a patient management system including an external device 2490, a telecommunication network 2491, and a remote device 2492. External device 2490 is placed within the vicinity of an IMD (s) and includes external telemetry system 2493 to communicate with the IMD. Remote device(s) 2492 is in one or more remote locations and communicates with external device 2490 through network 2491, thus allowing a physician or other caregiver to monitor and treat a patient from a distant location and/or allowing access to various treatment resources from the one or more remote locations. The illustrated remote device 2492 includes a user interface 2494. According to various embodiments, the external device includes a programmer or other device such as a computer, a personal data assistant or phone. The external device 2490, in various embodiments, includes two devices adapted to communicate with each other over an appropriate communication channel, such as a computer and a Bluetooth enabled portable device (e.g. personal digital assistant, phone), by way of example and not limitation.

Advanced patient management (APM) systems can be used to enable the patient and/or doctor to adjust parameter(s) to avoid observed or sensed habituation, or to adjust therapy intensity. The inputs can be provided by computers, programmers, cell phones, personal digital assistants, and the like. The patient can call a call center using a regular telephone, a mobile phone, or the internet. The communication can be through a repeater. In response, the call center (e.g. server in call center) can automatically send information to the device to adjust or titrate the therapy. The call center can inform the patient's physician of the event. A device interrogation can be automatically triggered. The results of the device interrogation can be used to determine if and how the therapy should be adjusted and/or titrated to improve the transient response. A server can automatically adjust and/or titrate the therapy using the results of the device interrogation. Medical staff can review the results of the device interrogation, and program the device through the remote server to provide the desired therapy adjustments and/or titrations. The server can communicate results of the device interrogation to the patient's physician, who can provide input or direction for adjusting and/or titrating the therapy.

Figure 25:
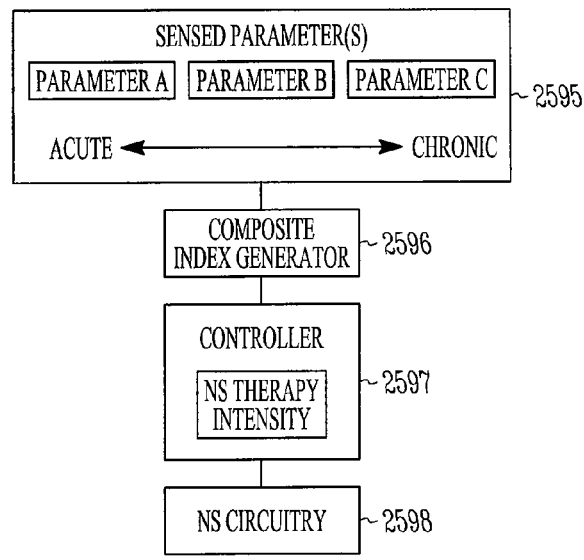
FIG. 25 illustrates a system embodiment that implements a neural stimulation protocol using a composite index of parameters of varying time responses.

FIG. 25 illustrates a system embodiment that implements a neural stimulation protocol using a composite index of parameters of varying time responses. A number of parameters are sensed, as illustrated at 2595, including parameters A, B and C. Each of these sensed parameters are associated with a time response to a change in autonomic health (e.g. a change in autonomic balance). In the illustrated embodiment, parameter A has a more acute response to a change in autonomic health than parameter B or C. The composite index generator 2596 receives values, such as sensed measurements or derived values based on sensed measurements, for these parameters, and generates the composite index according to a predetermined algorithm that weights the parameters according to, at least in part, the time response of the parameter to a change in autonomic health. The controller 2597 determines the desired neural stimulation intensity based on the composite index, and instructs the neural stimulation circuitry 2598 to appropriately adjust the neural stimulation intensity. For example, the amplitude, frequency or duration of a neural stimulation pulse train may be adjusted to adjust the neural stimulation intensity.

Figure 26:
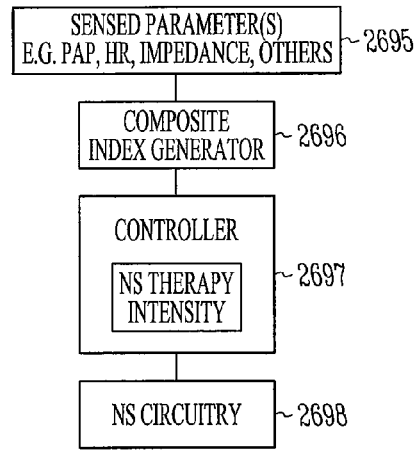
FIG. 26 illustrates a system embodiment that implements a neural stimulation protocol using a composite index of pulmonary artery pressure, heart rate, impedance, and other parameters.

FIG. 26 illustrates a system embodiment that implements a neural stimulation protocol using a composite index of pulmonary artery pressure, heart rate, impedance, and other parameters. The illustrated embodiment is similar to FIG. 25. FIG. 26 illustrates that pulmonary artery pressure, heart rate and impedance are sensed parameters with different time response. Heart rate has a relatively fast response, pressure has a response slower than heart rate, and impedance has a response slower than pressure. Thoracic impedance, for example, can be used to detect pulmonary edema, an indicator of decompensation. Impedance also can measure a change in cardiac contractility. These parameters can provide useful information concerning the acute and chronic autonomic health of the patient.

Figure 27:
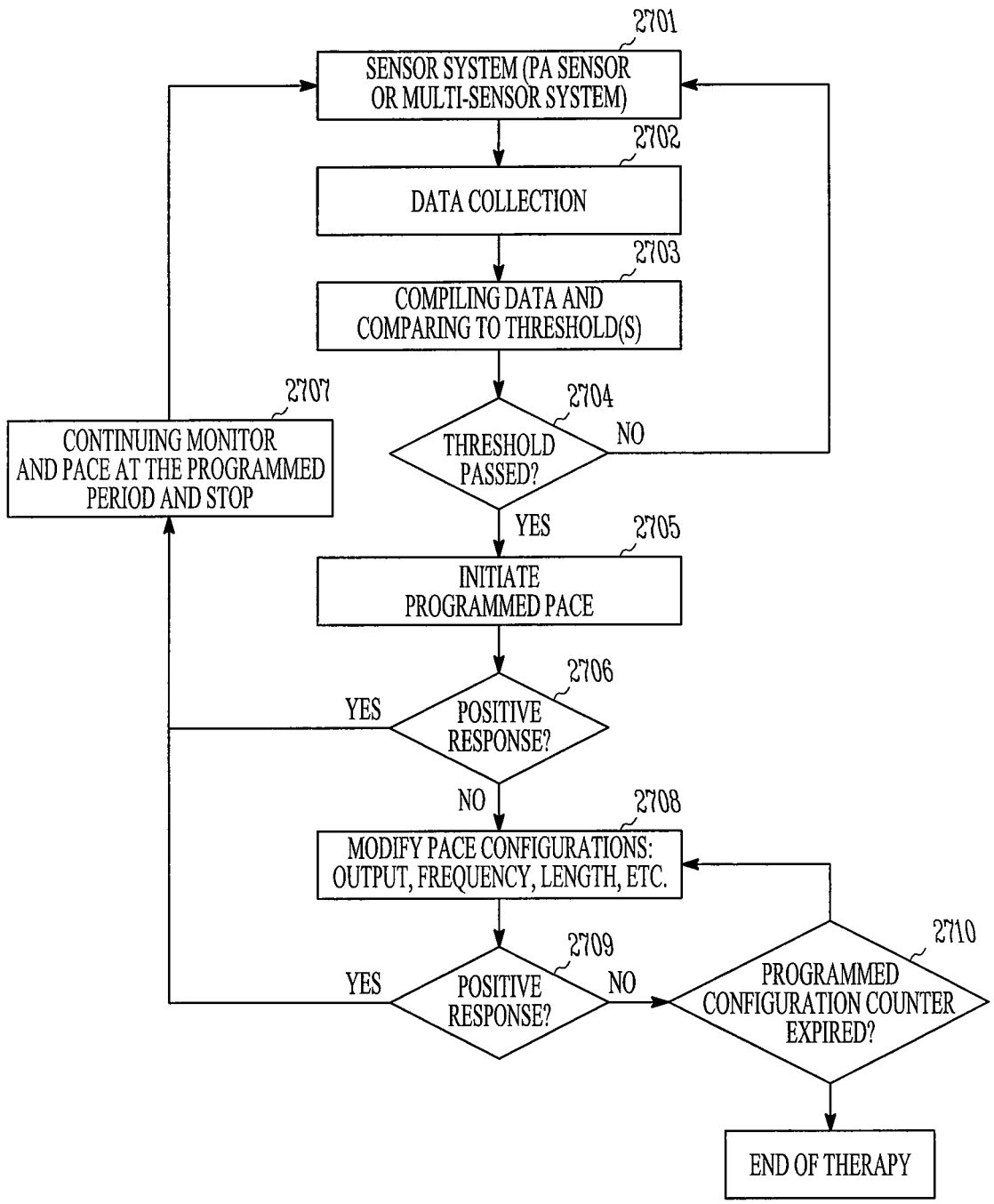
FIG. 27 illustrates a method for determining a threshold used to initiate a neural stimulation therapy.

FIG. 27 illustrates a method for determining a threshold used to initiate a neural stimulation therapy. As illustrated at 2701, a sensor system, such as a PA pressure sensor or a multi-sensor system, is used to sense physiological parameter(s). The system collects the data, as illustrated at 2702, and compiles the data into an index and compares the index to a threshold or thresholds for the index, as illustrated at 2703. The threshold can be a threshold at which a neural stimulation therapy is initiated. The threshold can be a threshold at which neural stimulation is adjusted. In the illustrated embodiment, if the threshold is passed at 2704, the neural stimulation therapy is initiated at 2705. Sensor(s) monitor the physiological response to the neural stimulation. If the response is positive, as determined at 2706, monitoring of the parameter(s) is continued, and the neural stimulation continues for programmed schedule of stimulation, as illustrated at 2707. If the response is not positive, as determined at 2706, one or more parameter(s) of the neural stimulation (amplitude, frequency, duty cycle, pulse train duration, etc.) are modified, as illustrated at 2708, until a positive response is detected at 2709 or until a counter expires, as illustrated at 2710.

Figure 28:
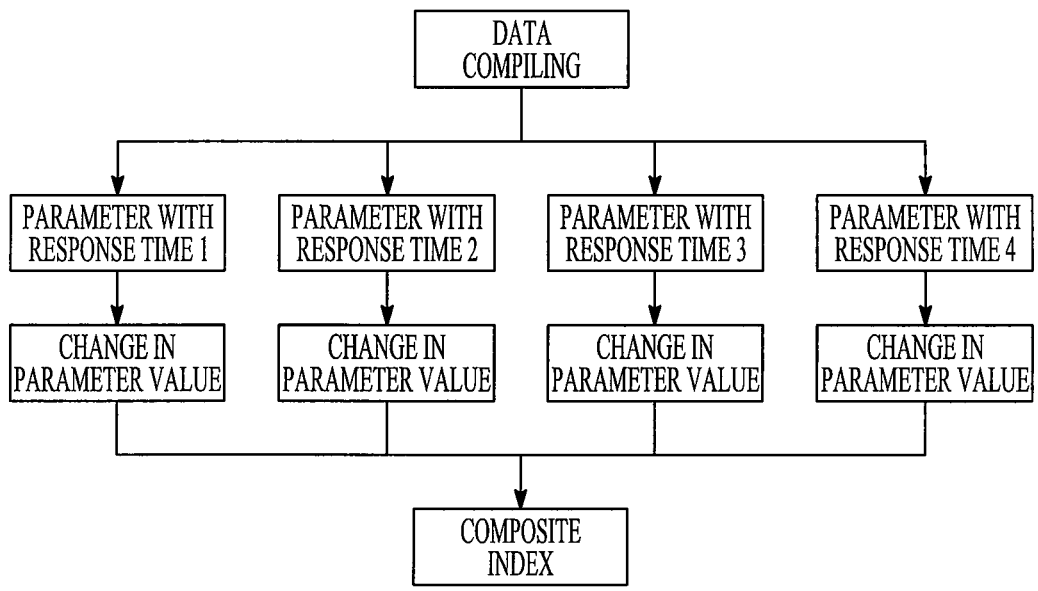
FIG. 28 illustrates a method for determining a composite index used in implementing a neural stimulation protocol.

FIG. 28 illustrates a method for determining a composite index used in implementing a neural stimulation protocol. The illustrated figure indicates that the monitored parameters have different response times to a change in autonomic health. The data compiling determines a change in each of the parameter, and then weights each parameter change based, at least in part, on the parameter's time response to a change in the autonomic balance. The composite index is generated using the weighted parameter changes. For example, some embodiments may provide more weight to changes in parameters with a fast response than parameters with a slow response, and some embodiments may provide more weight to changes in parameters with a slow response than parameters with a fast response. The parameters could be weighted based on importance or relevance assigned by a physician or determined by algorithm in addition to time response to change in autonomic balance.

Figure 29:
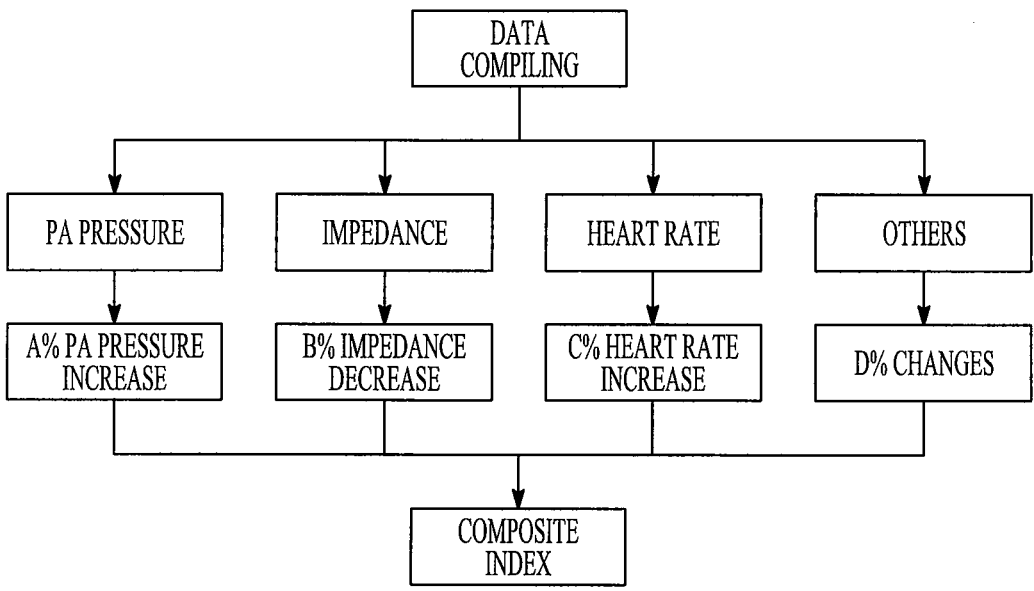
FIGS. 29 and 30 illustrate methods for weighting parameters, including PA pressure, impedance and heart rate, to determine a composite index used in implementing a neural stimulation protocol.
Figure 30:
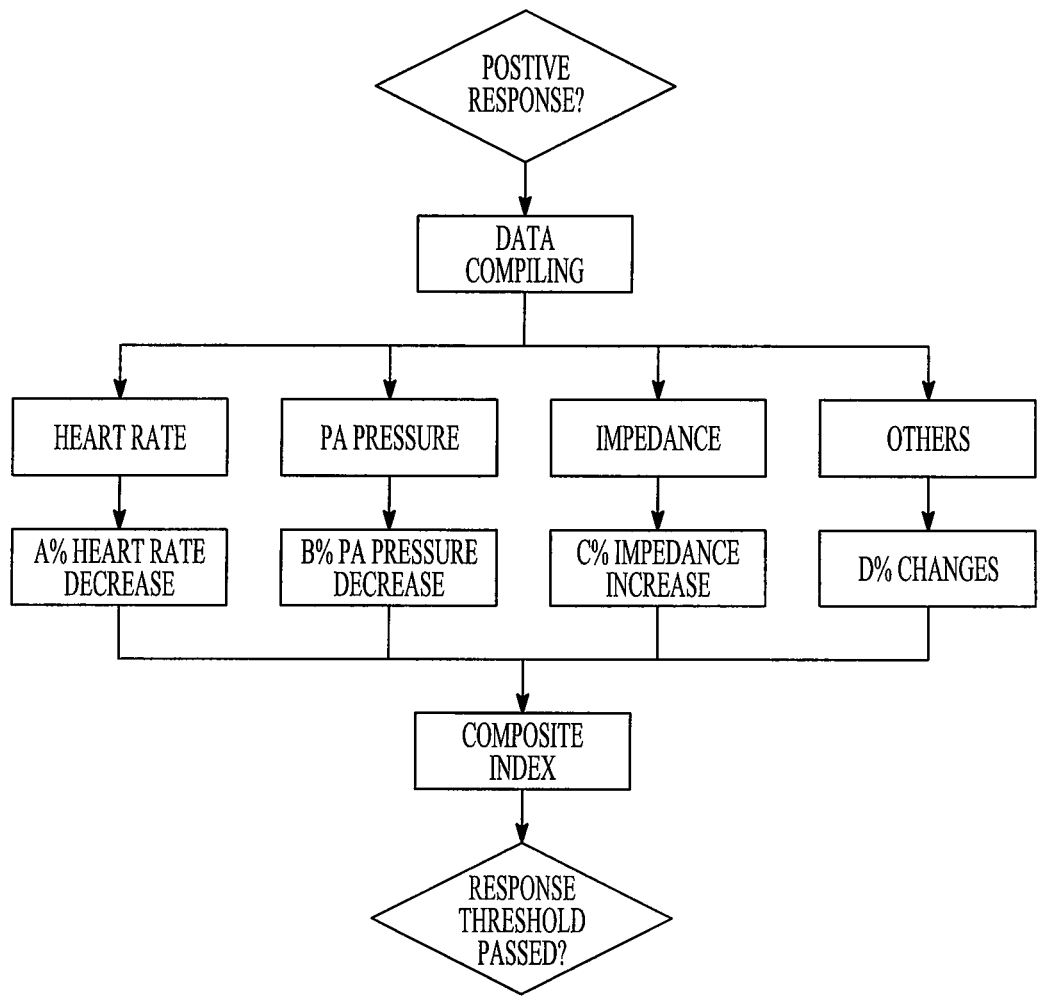

FIGS. 29 and 30 illustrate methods for weighting parameters, including PA pressure, impedance and heart rate, to determine a composite index used in implementing a neural stimulation protocol. These figures illustrate specific examples of the method illustrated in FIG. 28. In these figures, A % is larger than or equal to B %, which is larger than or equal to C %, which is larger than or equal to D %. As illustrated in FIG. 29, more weight is given to changes in pulmonary pressure than changes in heart rate. As illustrated in FIG. 30, more weight is given to decreased heart rate changes (a fast response) than to increased impedance changes (a slow response). The method illustrated in FIG. 29 can be used, for example, to generate a composite index to determine whether to initiate a neural stimulation therapy. The method illustrated in FIG. 30 can be used, for example, to detect whether the neural stimulation therapy is providing the desired response.

The systems can be designed to stimulate nerve traffic (providing a parasympathetic response when the vagus is stimulated), or to inhibit nerve traffic (providing a sympathetic response when the vagus is inhibited). Various embodiments deliver unidirectional stimulation or selective stimulation of some of the nerve fibers in the nerve. According to various embodiments, the device, as illustrated and described above, is adapted to deliver neural stimulation as electrical stimulation. Other elements for delivering neural stimulation can be used. For example, some embodiments use transducers to deliver neural stimulation using other types of energy, such as ultrasound, light, magnetic or thermal energy.

One of ordinary skill in the art will understand that, the modules and other circuitry shown and described herein can be implemented using software, hardware, and combinations of software and hardware. As such, the terms module and circuitry, for example, are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined. In various embodiments, the methods are implemented using a computer data signal embodied in a carrier wave or propagated signal, that represents a sequence of instructions which, when executed by one or more processors cause the processor(s) to perform the respective method. In various embodiments, the methods are implemented as a set of instructions contained on a computer-accessible medium capable of directing a processor to perform the respective method. In various embodiments, the medium is a magnetic medium, an electronic medium, or an optical medium.

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device for stimulating an autonomic neural target from within a pulmonary artery, comprising:
   at least one electrode;
   a power supply;
   a neural stimulator connected to the power supply, and configured to generate a neural stimulation signal for delivery to the neural stimulation target through the at least one electrode; and
   an anchor structure configured to chronically and securely implant the neural stimulator, the power supply and the at least one electrode within the pulmonary artery,
   wherein the neural stimulator is configured to implement the neural stimulation protocol to:

sense at least two physiological parameters indicative of autonomic health which can be used as a control input for delivering neural stimulation, wherein the at least two parameters have different time responses to a change in the autonomic health such that a first physiological parameter provides an indication of autonomic health that is more acute than a second physiological parameter;

generate a composite index using the at least two physiological parameters, including weighting each of the at least two physiological parameters based at least in part on each parameter's time response; and use the composite index to control delivery of the neural stimulation.

2. The device of claim 1, wherein the anchor structure, the neural stimulator, the power supply and the at least one electrode are configured to be implanted through a pulmonary valve into the pulmonary artery, and the neural stimulator is configured to be operational to implement a neural stimulation protocol when chronically implanted within the pulmonary artery without a wired connection through the pulmonary valve.

3. The device of claim 1, wherein the neural stimulator includes a control system configured to implement the neural stimulation protocol.

4. The device of claim 1, wherein the neural stimulator includes a communication module adapted to wirelessly receive instructions from a controller outside of the pulmonary artery to implement the neural stimulation protocol.

5. The device of claim 1, further comprising:
a pressure sensor configured to sense a pulmonary artery pressure or a heart rate sensor configured to sense heart rate; and
the neural stimulator is connected to the pressure sensor or heart rate sensor, and configured to control the neural stimulation protocol based on a sensed pulmonary artery pressure or a sensed heart rate.

6. The device of claim 5, wherein the neural stimulator is configured to derive heart rate from sensed pulmonary artery pressure.

7. The device of claim 1, wherein the neural stimulator is configured to generate the composite index using at least two parameters selected from the group of parameters consisting of: a heart rate parameter, an impedance parameter, and a pulmonary artery pressure parameter.

8. The device of claim 1, wherein the anchor structure, the neural stimulator and the at least one electrode are configured to deliver neural stimulation targeted to stimulate baroreceptors in the pulmonary artery.

9. The device of claim 1, wherein the power supply includes a rechargeable battery, and means for wirelessly recharging the rechargeable battery.

10. The device of claim 1, wherein the at least one electrode is integrally formed with the anchor structure.

11. A system for stimulating baroreceptors in a pulmonary artery, comprising:
means for sensing at least one physiological parameter; and
at least one pulmonary artery device configured to be delivered through a pulmonary valve in the pulmonary artery, including:
a power supply for providing power to the at least one pulmonary artery device;
means for stimulating the autonomic neural target from within the pulmonary artery; and
means for chronically and securely implanting the at least one pulmonary artery device within the pulmonary artery;
means for sensing at least two physiological parameters indicative of autonomic health which can be used as a control input for delivering neural stimulation, wherein the at least two parameters have different time responses to a change in the autonomic health such that a first physiological parameter provides an indication of autonomic health that is more acute than a second physiological parameter;
means for generating a composite index using the at least two physiological parameters, including weighting each of the at least two physiological parameters based at least in part on each parameter's time response; and
means for implementing a neural stimulation therapy, including means for using the composite index to control delivery of the neural stimulation.

12. The system of claim 11, further comprising means for performing a pacing therapy.

13. The system of claim 11, wherein the means for sensing includes a pulmonary artery pressure sensor configured to be chronically implanted into the pulmonary artery.

14. The system of claim 11, wherein the means for sensing includes means for sensing heart rate, impedance, heart sounds, respiration, blood flow, posture or activity.

15. The system of claim 11, wherein the means for sensing includes means for sensing using an implantable sensor outside of the pulmonary artery, and the at least one pulmonary artery device includes means for wirelessly communicating from within the pulmonary artery to the implantable sensor outside of the pulmonary artery.

16. The system of claim 11, wherein the at least one pulmonary artery device includes a first device configured to be implanted in a right pulmonary artery and a second device configured to be implanted in a left pulmonary artery, wherein the first and second device include means for communicating between each other.

17. The system of claim 11, wherein the neural stimulation therapy includes heart failure therapy, and the means for implementing a neural stimulation therapy includes means for stimulating baroreceptors within the pulmonary artery to treat heart failure.

18. The system of claim 11, wherein the means for implementing a neural stimulation protocol when chronically implanted within the pulmonary artery without a wired connection through the pulmonary artery includes means for controlling the neural stimulation from within the pulmonary artery or means for controlling the neural stimulation from outside of the pulmonary artery.

19. The system of claim 11, wherein the neural stimulation therapy includes ischemia therapy, and the means for implementing a neural stimulation therapy includes means for stimulating baroreceptors within the pulmonary artery to treat ischemia.

20. The system of claim 11, wherein the neural stimulation therapy includes an arrhythmia therapy, and the means for implementing a neural stimulation therapy includes means for stimulating baroreceptors within the pulmonary artery to treat arrhythmia.

21. The system of claim 11, wherein the neural stimulation therapy includes hypertension therapy, and the means for implementing a neural stimulation therapy includes means for stimulating baroreceptors within the pulmonary artery to treat hypertension.

22. The system of claim 11, further comprising means for performing an antitachycardia therapy.

23. The system of claim 11, further comprising means for performing a cardiac resynchronization therapy.

* * * * *